US011435351B2

(12) United States Patent
Tucker

(10) Patent No.: US 11,435,351 B2
(45) Date of Patent: Sep. 6, 2022

(54) METHODS FOR DETERMINING VACCINE POTENCY

(71) Applicant: BIOMADISON, INC., Del Mar, CA (US)

(72) Inventor: Ward C Tucker, Monona, WI (US)

(73) Assignee: BioMadison, Inc., Del Mar, CA (US)

(*) Notice: Subject to any disclaimer, the term of this patent is extended or adjusted under 35 U.S.C. 154(b) by 0 days.

(21) Appl. No.: 16/387,389

(22) Filed: Apr. 17, 2019

(65) Prior Publication Data

US 2019/0339273 A1 Nov. 7, 2019

Related U.S. Application Data

(60) Provisional application No. 62/799,457, filed on Jan. 31, 2019, provisional application No. 62/734,866, filed on Sep. 21, 2018, provisional application No. 62/659,592, filed on Apr. 18, 2018.

(51) Int. Cl.
*G01N 33/53* (2006.01)
*G01N 33/50* (2006.01)
*G01N 33/569* (2006.01)
*C12N 5/0781* (2010.01)
*G01N 33/94* (2006.01)

(52) U.S. Cl.
CPC ..... *G01N 33/56983* (2013.01); *C12N 5/0635* (2013.01); *G01N 33/5052* (2013.01); *G01N 33/94* (2013.01); *G01N 2469/10* (2013.01)

(58) Field of Classification Search
CPC ........ A61K 38/00; A61K 39/00; A61K 39/02; A61K 39/39; A61K 39/35; A61K 39/395
USPC ..... 424/9.1, 9.2, 130.1, 184.1, 278.1; 435/4, 435/41, 174, 243
See application file for complete search history.

(56) References Cited

U.S. PATENT DOCUMENTS

| 9,057,716 B2 | 6/2015 | Balocchi et al. |
| 2005/0277109 A1 | 12/2005 | Ennis |
| 2009/0075304 A1 | 3/2009 | Weidanz |
| 2011/0091984 A1 | 4/2011 | Williams |
| 2014/0141455 A1 | 5/2014 | Weidanz |
| 2015/0301051 A1 | 10/2015 | Giuliani |

FOREIGN PATENT DOCUMENTS

| WO | 2012025612 | 3/2012 |
| WO | 2017005880 | 1/2017 |

OTHER PUBLICATIONS

Hans Draayer, Procedia in Vaccinology, 2011, 5:171-174. (Year: 2011).*
Coenraad FM Hendriksen, Expert Rev. Vaccines, 2008, 8(3):313-322. (Year: 2008).*
Extended European Search report dated Dec. 20, 2021, from related European application No. 19788047.9. 7 pages.
Gupta, Sachin, et al. "DNA vaccine molecular adjuvants SP-D-BAFF and SP-D-APRIL enhance anti-gp120 immune response and increase HIV-1 neutralizing antibody tiers," Jpurmnal of Virology. vol. 89, No. 8, Apr. 2015. 12 pages.
Verch, Thorsten, et al. "Principles of vaccine potency assays," Bioanalysis. 10(3), 163-180, 2018. 18 Pages.
PCT Search report dated Aug. 9, 2019, from related PCT application No. PCT/US2019/027963. 6 pages.
Mobs, et al. "Research Techniques Made Simple: Monitoring of T-Cell Subsets using the ELISPOT Assay,"Department of Dermatology and Allergology, Philipps University Marburg. 2016. 5 pages.

* cited by examiner

*Primary Examiner* — Stacy B Chen
(74) *Attorney, Agent, or Firm* — Fish IP Law, LLP

(57) ABSTRACT

Compositions and methods for determining the efficacy and/or potency of a vaccine preparation are described herein. Splenocytes from immunized animals are isolated and frozen. Upon thawing aliquots these cells are activated by exposure to a series of dilutions of q vaccine preparation being tested and a series of dilutions of a reference vaccine with known characteristics. Cells secreting immunogen-specific antibody and cells secreting nonspecific antibody are enumerated, as is the amount of immunogen-specific and nonspecific antibody produced. Comparison between the results from the vaccine preparations provides a measure of relative vaccine efficacy and/or potency.

11 Claims, 22 Drawing Sheets

5e4 cells 2.5e4 cells

1e4 cells

5e3 cells

FIG. 5A

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B |   | Negative Control | SC1 0.03 pM | SC1 0.1 pM | SC1 0.3 pM | SC1 1 pM | SC1 3 pM | SC1 10 pM | SC1 30 pM | SC1 100 pM | SC1 300 pM |   |
| C | Total splenocytes | Negative Control | TS1 0.03 pM | TS1 0.1 pM | TS1 0.3 pM | TS1 1 pM | TS1 3 pM | TS1 10 pM | TS1 30 pM | TS1 100 pM | TS1 300 pM |   |
| D |   | SC1 300 pM | SC1 100 pM | SC1 30 pM | SC1 10 pM | SC1 3 pM | SC1 1 pM | SC1 0.3 pM | SC1 0.1 pM | SC1 0.03 pM | Negative Control |   |
| E |   | TS1 300 pM | TS1 100 pM | TS1 30 pM | TS1 10 pM | TS1 3 pM | TS1 1 pM | TS1 0.3 pM | TS1 0.1 pM | TS1 0.03 pM | Negative Control |   |
| F |   | Negative Control | SC1 0.03 pM | SC1 0.1 pM | SC1 0.3 pM | SC1 1 pM | SC1 3 pM | SC1 10 pM | SC1 30 pM | SC1 100 pM | SC1 300 pM |   |
| G |   | Negative Control | TS1 0.03 pM | TS1 0.1 pM | TS1 0.3 pM | TS1 1 pM | TS1 3 pM | TS1 10 pM | TS1 30 pM | TS1 100 pM | TS1 300 pM |   |
| H |   |   |   |   |   |   |   |   |   |   |   |   |

FIG. 6A

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B |   | Negative Control | SC1 0.3 pM | SC1 1 pM | SC1 3 pM | SC1 10 pM | SC1 30 pM | SC1 100 pM | SC1 300 pM | SC1 1000 pM | SC1 3000 pM |   |
| C | total splenocytes | Negative Control | TS1 0.3 pM | TS1 1 pM | TS1 3 pM | TS1 10 pM | TS1 30 pM | TS1 100 pM | TS1 300 pM | TS1 1000 pM | TS1 3000 pM |   |
| D |   | SC1 3000 pM | SC1 1000 pM | SC1 300 pM | SC1 100 pM | SC1 30 pM | SC1 10 pM | SC1 3 pM | SC1 1 pM | SC1 0.3 pM | Negative Control |   |
| E |   | TS1 3000 pM | TS1 1000 pM | TS1 300 pM | TS1 100 pM | TS1 30 pM | TS1 10 pM | TS1 3 pM | TS1 1 pM | TS1 0.3 pM | Negative Control |   |
| F |   | Negative Control | SC1 0.3 pM | SC1 1 pM | SC1 3 pM | SC1 10 pM | SC1 30 pM | SC1 100 pM | SC1 300 pM | SC1 1000 pM | SC1 3000 pM |   |
| G |   | Negative Control | TS1 0.3 pM | TS1 1 pM | TS1 3 pM | TS1 10 pM | TS1 30 pM | TS1 100 pM | TS1 300 pM | TS1 1000 pM | TS1 3000 pM |   |
| H |   |   |   |   |   |   |   |   |   |   |   |   |

FIG. 7A

METHODS FOR DETERMINING VACCINE POTENCY

This application claims the benefit of U.S. Provisional Application No. 62/799,457, filed Jan. 31, 2019, U.S. Provisional Application No. 62/734,866, filed Sep. 21, 2018, and U.S. Provisional Application No. 62/659,592 filed on Apr. 18, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is vaccines, specifically methods for determining immunogenicity and/or potency of prophylactic and/or preventative vaccine preparations.

BACKGROUND

The background description includes information that may be useful in understanding the present invention. It is not an admission that any of the information provided herein is prior art or relevant to the presently claimed invention, or that any publication specifically or implicitly referenced is prior art.

Despite care taken during manufacture, the potency of vaccine preparations can vary from batch to batch. Accordingly, potency of individual batches needs to be determined in order to assure that the vaccine can provide the needed immune response. Traditionally this is determined using immunodiffusion assays. In these assays a gel matrix (typically agarose blended with antibodies directed to a vaccine antigen) is prepared and cast on a support. Portions of the gel matrix are removed to generate test wells, into which samples of the vaccine preparation and quantified standards are placed. Diffusion of antigens progresses outwards from these test wells and when the proportion of antigen to antibody is correct a visible precipitate forms. This distance of this precipitate from the test well is proportional to the antigen concentration of the sample placed in the well. While effective at identifying antibody-reactive materials in a vaccine preparation such an approach to quantitation of potency is relatively slow and can be somewhat subjective. In addition, at best this approach only serves to characterize the antigen to which the specific antibody used is directed and does not provide a direct indication of immunogenicity of the vaccine preparation.

Other approaches to evaluating vaccine potency have been suggested. U.S. Pat. No. 9,057,716 (to Balocchi et al.) and United States Patent Application Publication No. 2015/0301051 (to Giuliani and Mori) describe using an enzyme immunoassay incorporating bactericidal antibodies directed to meningococcal antigens to characterize the potency of meningococcal vaccines. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Such an approach, however, merely quantifies the amount of these specific antigens in a vaccine preparation, and does not provide a direct measure of immunogenicity of the intact preparation.

International Patent Application Publication No. WO 2017005880 (to Wen et al.) describes an attempt to characterize immunogenicity of influenza vaccines, based on differences in the sensitivity of HA antigens that have been denatured during processing and those that have retained their native conformation to trypsin digestion. The described method continues to rely on immunodiffusion, however, and retains the limitations of that approach. In addition it is not apparent that this approach can be used with a broad variety of vaccines.

United States Patent Application Publication No. 2014/0141455 (to Weidanz) describes a method of determining vaccine potency by using a highly specific antibody directed to a peptide-HLA complex to visualize the density of such peptide-HLA complexes on the surfaces of antigen-presenting cells. Such an approach, however, is dependent on the ability to generate the requisite antibodies, and at best provides a measure of the extent of antigen presentation and not a measure of the potency of the intact vaccine preparation.

Thus, there is still a need for methods for directly assessing immunogenicity and/or potency of vaccine preparations.

SUMMARY OF THE INVENTION

The inventive subject matter provides compositions and methods for determining the relative potency of vaccine compositions. Splenocytes from immunized mice are collected, and optionally CD138 depleted prior to freezing. To determine the potency of a vaccine preparation a portion of the frozen splenocytes are thawed and then activated using serial dilutions of a test vaccine preparation and a control vaccine preparation of known potency. The number of cells expressing antibody specific for the immunizing antigen is determined for each dilution (in some instances relative to the total number of cells producing antibodies) and the resulting dose-response curves used to determine potency of the test vaccine.

One embodiment of the inventive concept is a method of characterizing potency of a vaccine preparation by vaccinating an animal with a reference vaccine, collecting splenocytes or B cells from the animal, exposing a portion of the splenocytes or B cells to a first set of serial dilutions of the reference vaccine, exposing another portion of the splenocytes or B cells to second set of serial dilutions of the vaccine preparation, determining how many cells from the portion exposed to the reference vaccine are expressing antibodies specific for an antigen of the vaccine preparation relative to the dilutions of the reference vaccine, determining how many cells from the portion exposed to the reference vaccine are expressing nonspecific antibodies relative to the dilutions of the reference vaccine, determining how many cells from the portion exposed to the test vaccine are expressing antibodies specific for the antigen relative to the dilutions of the test vaccine, determining how many cells in the portion exposed to the test vaccine are expressing nonspecific antibodies relative to the dilutions of the test vaccine comparing the antigen-specific results from the cells exposed to the reference vaccine and the test vaccine. In some embodiments the nonspecific antibody results from the cells exposed to the reference vaccine and to the test vaccine are also compared. In some embodiments the results for antigen-specific antibodies and for nonspecific antibodies are determined on the same test surface; in such embodiments methods used to determine antigen-specific and non-specific antibodies can use localized, differentiable labels. In some embodiments the ratio of antigen-specific to nonspecific antibodies for two or more of a set of serial dilutions for cells exposed to the reference vaccine and for cells exposed to the test vaccine can be used as a basis for comparison. The relationship between a function describing the relationship between such ratios relative to the corresponding reference vaccine dilutions (e.g. a first slope) and a different function describing the relationship between such ratios relative to the corresponding test vaccine dilutions (e.g. a second slope) can be used as a basis for comparison.

In some embodiments of the inventive concept the vaccine preparation being characterized can include a second vaccinating antigen. In such embodiments a portion of the collected splenocytes or B cells are exposed to a third set of serial dilutions of the reference vaccine, and another portion of the splenocytes or B cells are exposed to a fourth set of serial dilutions of the vaccine preparation. The number of cells from the portion exposed to the reference vaccine that are expressing antibodies specific for the second antigen of the vaccine preparation relative to the dilutions of the reference vaccine is determined, as well as the number cells from the portion exposed to the reference vaccine that are expressing nonspecific antibodies relative to the dilutions of the reference vaccine. Similarly, the number of cells from the portion exposed to the test vaccine that are expressing antibodies specific for the second antigen relative to the dilutions of the test vaccine is determined, as well as the number of cells in the portion exposed to the test vaccine that are expressing nonspecific antibodies relative to the dilutions of the test vaccine. Second antigen-specific results from the cells exposed to the reference vaccine and to the test vaccine are then compared. In some embodiments the nonspecific antibody results from the cells exposed to the reference vaccine and to the test vaccine are also compared. In some embodiments the results for the second antigen specific antibodies and for nonspecific antibodies are determined on the same test surface; in such embodiments methods used to determine second antigen specific and nonspecific antibodies can use localized, differentiable labels. In some embodiments testing for the first antigen specific antibodies, second antigen specific antibodies, and nonspecific antibodies are performed on the same test surface. In such embodiments mutually differentiable and localizable labels can be used to distinguish between first antigen specific, second antigen specific, and nonspecific antibody results. In some embodiments the ratio of second antigen specific to nonspecific antibodies for two or more of a set of serial dilutions for cells exposed to the reference vaccine and for cells exposed to the test vaccine can be used as a basis for comparison. The relationship between a function describing the relationship between such ratios relative to the corresponding reference vaccine dilutions (e.g. a third slope) and a different function describing the relationship between such ratios relative to the corresponding test vaccine dilutions (e.g. a fourth slope) can be used as a basis for comparison.

In some embodiments of the inventive concept the vaccine preparation includes preventative vaccine. Such a preventative vaccine can be directed to an adenovirus, anthrax, botulism, cholera, diphtheria, hepatitis A, hepatitis B, hepatitis C, *Haemophilus influenza* type b, a human papillomavirus, a seasonal influenza, Japanese encephalitis, measles, Meningococcus, mumps, pertussis, Pneumoccocus, polio, rabies, a rotavirus, rubella, shingles, smallpox, tetanus, tuberculosis, typhoid fever, varicella, and/or yellow fever. In some embodiments the vaccine preparation includes a therapeutic vaccine. Such a therapeutic vaccine can be directed to glioblastoma, cervical cancer, skin cancer, lung cancer, breast cancer, head and neck cancer, pancreatic cancer, celiac disease, and/or vulvovaginal candidiasis.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 schematically depicts a conventional prior art antibody plaque immunoassay.

FIG. 2 shows typical results from a prior art antibody plaque immunoassay, showing results in terms of spot forming cells (SFC) among tumor infiltrating lymphocytes (TLIs) identified by a prior art antibody plaque immunoassay under control conditions (−), stimulation with the known survivin-derived epitope SUR53-62, and several irrelevant peptides (1, 2, 3).

FIG. 3 provides a flow chart of an exemplary protocol for using splenocytes to determine vaccine potency.

FIG. 4A is a scanned image of an HcR/A antigen antibody plaque immunoassay plate from a splenocytes assay of the inventive concept. Splenocytes are coated at either $5\times10^4$ (top left quadrant), $2.5\times10^4$ (top right quadrant), $10^4$ (bottom left quadrant), or $5\times10^3$ (bottom right quadrant) cells/well.

FIG. 4B shows typical dose response curves generated by data derived from the plate shown in FIG. 4A. TS=test sample of HcR/A preparation, SC=control sample of HcR/A preparation.

FIG. 4C shows an example of relative potency of test and reference antigen preparations as determined by a method of the inventive concept.

FIG. 5A: FIG. 5A shows an example of a test antibody plaque immunoassay plate layout for use in a method of the inventive concept.

FIG. 5B depicts a scanned image of an antibody plaque immunoassay plate prepared as in FIG. 5A in which IgG secretion by stimulated splenocytes is visualized.

FIG. 5C depicts a scanned image of an antibody plaque immunoassay plate prepared as in FIG. 5A in which HcR/A specific antibody secretion by stimulated splenocytes is visualized.

FIG. 5D provides a magnified view of a typical individual well from an antibody plaque immunoassay plate.

FIG. 5E shows dose response curves, calculated $EC_{50}$, and calculated relative potency for IgG secretion from splenocytes in an ELISpot plate prepared as in FIG. 5A.

FIG. 5F shows dose response curves, calculated $EC_{50}$, and calculated relative potency for HcR/A specific antibody secretion from splenocytes in an antibody plaque immunoassay plate prepared as in FIG. 5A.

FIG. 6A: FIG. 6A shows an example of a test antibody plaque immunoassay plate layout for use in a splenocytes vaccine potency assay of the inventive concept.

FIG. 6B provides a scanned image of an antibody plaque immunoassay plate prepared as in FIG. 6A in which IgG secretion by stimulated splenocytes is visualized.

FIG. 6C provides a scanned image of an antibody plaque immunoassay plate prepared as in FIG. 6A in which HcR/A specific antibody secretion by stimulated splenocytes is visualized.

FIG. 6D shows dose response curves, calculated $EC_{50}$, and calculated relative potency for IgG secretion from splenocytes in an antibody plaque immunoassay plate prepared as in FIG. 6A.

FIG. 6E shows dose response curves, calculated $EC_{50}$, and calculated relative potency for HcR/A specific antibody secretion from splenocytes in an antibody plaque immunoassay plate prepared as in FIG. 6A.

FIG. 7A: FIG. 7A shows an example of a test microwell plate layout for use in determining vaccine potency using a splenocyte assay of the inventive concept.

FIG. 7B provides a scanned image of an antibody plaque immunoassay plate prepared as in FIG. 7A in which IgG secretion by stimulated splenocytes is visualized.

FIG. 7C provides a scanned image of an antibody plaque immunoassay plate prepared as in FIG. 7A in which HcR/A specific antibody secretion by stimulated splenocytes is visualized.

FIG. 7D shows dose response curves, calculated $EC_{50}$, and calculated relative potency for IgG secretion from splenocytes in an ELISpot plate prepared as in FIG. 7A from splenocytes activated at different cell densities.

FIG. 7E shows dose response curves, calculated $EC_{50}$, and calculated relative potency for HcR/A specific antibody secretion from splenocytes in an antibody plaque immunoassay plate prepared as in FIG. 7A from splenocytes activated at different cell densities.

DETAILED DESCRIPTION

Figure 1:
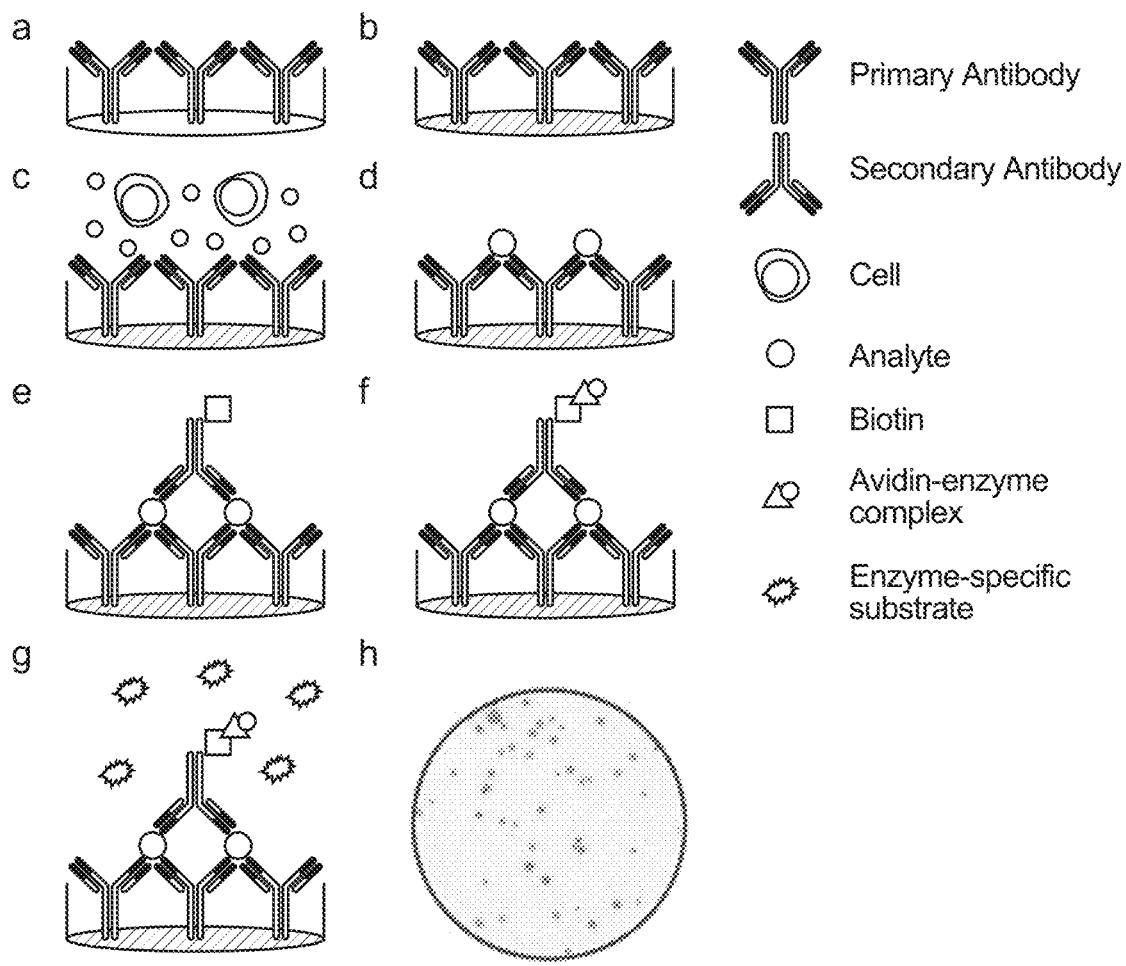
FIG. 1.

The following description includes information that may be useful in understanding the present invention. It is not an admission that any of the information provided herein is prior art or relevant to the presently claimed invention, or that any publication specifically or implicitly referenced is prior art.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The inventive subject matter provides compositions and methods in which mice or similar test animals are vaccinated with a reference batch of a vaccine that is known to be immunogenic and have acceptable potency. Splenocytes and/or B-cells are obtained from the vaccinated animals, and in some embodiments B-cell populations of such samples can be enriched or depleted (e.g. depletion of extant plasma cells). Suitable cells can be obtained by a variety of means, including dissection and/or perfusion of the spleen, dissection of one or more lymph nodes, and/or collection from circulation. Splenocytes or B cells can be isolated using antibody-coated magnetic beads, fluorescence activated cell sorting, or any suitable method. Following isolation, cells can be used immediately or permitted to replicate prior to use. In some embodiments isolated cells can be stored (for example, stored at about −80° C., or liquid or gas phase liquid nitrogen) prior to use.

For testing, the cells are plated onto two sets of test sites or surfaces, one of which is used for characterizing secretion of antibodies directed to a vaccine antigen and another of which is used for characterization of the section of non-specific (i.e. not directed to a vaccine antigen) antibodies. Suitable test surfaces include slides, the surfaces of wells of microwell plates, beads, and/or surfaces of microfluidic devices.

Serial dilutions of a vaccine to be tested are applied to one set of cells, while serial dilutions of the reference vaccine are applied to a second set of cells. In some embodiments cells previously sensitized by exposure to a vaccine preparation (either in vivo or in vitro) are utilized in testing. In such embodiments these presensitized cells can be re-activated by exposure to test and/or control vaccine preparations in order to determine vaccine batch potency. In some embodiment such re-activation can be performed prior to application of the cells to methods for detection of antibody secretion (e.g. using an antibody plaque assay, such as ELISpot™) In other embodiments such re-activation can be performed during at least a portion of the performance of methods for detection of antibody secretion. The number of cells secreting vaccine antigen-specific antibodies is characterized (for example, using a sandwich assay directed to vaccine antigen-specific antibodies that generates a localized signal) as well as the number of cells secreting non-specific antibodies (for example, using a sandwich assay directed to a species-specific antibody that generates a localized signal).

The slope of the titration curve for the percentage of cells secreting vaccine antigen specific antibodies (relative to the response generated by cells stimulated using a reference lot of vaccine) can provide a direct measurement of the vaccine's potency (i.e. ability to induce an antigen-specific antibody response). For example, a comparison of dose response curves produced by titration of test and reference vaccine samples can provide a relative measure of vaccine potency, for example by comparing the dilution that provides a midpoint response (e.g. EC50, instant midpoint slope, etc.) in the respective titration curves. A comparison of such a value to that of reference vaccine provides a measure of the suitability of a test vaccine's suitability for use.

In some embodiments both specific and non-antigen specific antibodies produced in response to exposure to a vaccine preparation can be evaluated. In such embodiments the ability of a test vaccine to induce an antigen-specific response can be compared to a reference vaccine. The degree of nonspecific antibody response induced by a vaccine preparation can provide information related to the potency of non-antigen components of vaccine preparation (such as adjuvants). For example, the determination of the ratio of specific to nonspecific antibody response for a test vaccine can be compared to that of a reference vaccine to provide a determination of potency.

One should appreciate that the disclosed techniques provide many advantageous technical effects including providing a direct measurement of vaccine potency using relatively few test animals. For examples, splenocytes isolated from a single immunized mouse can be stored and used for multiple determinations. In addition, the described approach provides a measure of the immunogenicity/potency of the intact vaccine formulation (e.g. including vehicles and adjuvants), whereas prior art approaches only characterized specific components (e.g. vaccinating antigen). The Applicant notes that the approach is highly adaptable, and is not limited in regards to the range of vaccinating or antigenic species.

As noted above, an immunoassay can be used to enumerate and/or characterize B cells that are secreting antibodies having the desired specificity in response to exposure to a vaccine preparation. For example, secretion of antibodies to the desired antigen can be detected using surfaces (e.g. membranes) proximal to such cells that have been coated with anti-species antibody to capture secreted immunoglobulins in what are commonly referred to as ELISpot™ or antibody plaque assays. The captured immunoglobulins can then serve to capture a specific antigen (or a labeled analog thereof). Such captured specific antigens can be visualized, either using a second antigen-specific antibody (e.g. in a sandwich assay) or by visualizing a label attached to a captured antigen analog. Secretion of nonspecific antibodies can be detected in a similar fashion using pairs of species-specific antibodies. Alternatively, the amount of secreted antigen specific and/or nonspecific antibodies can be characterized from samples of cell culture media exposed to stimulated splenocytes, for example by immunoassay.

While antibody plaque assays are described, other methodologies can also be utilized. For example, a reverse hemolytic plaque assay can be used to both enumerate antibody secreting cells and provide an estimate of the amount of antibody being secreted. Exposure to either an Ig-specific antibody or a specific antigen (or suitable analog) prior to exposure to complement and subsequent negative plaque formation can provide differentiation between nonspecific and specific antibody secretion. Alternatively, samples can be split and antibody producing cells can be identified and enumerated using flow cytometry by labeling with either an anti-Ig antibody (for nonspecific antibody secretion) or an antigen or antigen analog (for antigen-specific antibody secretion) conjugated with a detectable label (e.g. a fluorescent compound). The amount of specific and/or nonspecific antibody produced in the remaining portion of such a split sample can be quantified using conventional immunoassay techniques. Results of cell enumeration and amount of specific and/or nonspecific antibody produced can be evaluated separately, or integrated to provide a value representative of both the number of cells and amount of immunoglobulin produced.

In an exemplary embodiments of an assay for detection of secreted antibodies directed to a specific antigen, the wells of a test plate are coated with the antigen of interest. Immunoglobulin secreting cells (e.g. splenocytes treated with a dilution of a vaccine preparation) are added to the plate and incubated for a period of time sufficient for secreted antibodies to form complexes with portions of the antigen-coated plate proximal to the cells. After a wash step a secondary antibody carrying a detectable label (e.g. horseradish peroxidase, alkaline phosphatase, a fluorophore, etc.) and directed against the secreted antibody species is added to the plate and allowed to complex with the secreted antibodies coupled to the plate via the immobilized antigen. After an additional wash step the label can be visualized (e.g. by addition of a precipitable chromogenic substrate or excitation with a suitable light frequency) and the sites where specific antibody secretion occurred enumerated. Enumeration can be performed manually or by image recognition software.

In an exemplar embodiments of an assay for detection of total secreted antibodies (i.e. both antigen specific and nonspecific), the wells of a test plate are coated with an antibody directed to the immunoglobulin species (e.g. anti-mouse IgG). Immunoglobulin secreting cells (e.g. splenocytes treated with a dilution of a vaccine preparation) are added to the plate and incubated for a period of time sufficient for secreted antibodies to form complexes with portions of the antibody-coated plate proximal to the cells. After a wash step a secondary antibody carrying a detectable label (e.g. horseradish peroxidase, alkaline phosphatase, a fluorophore, etc.) and directed against the secreted immunoglobulin species is added to the plate and allowed to complex with the secreted antibodies coupled to the plate via the immobilized anti-species antibody. After an additional wash step the label can be visualized (e.g. by addition of a precipitable chromogenic substrate or excitation with a suitable light frequency) and the sites where specific antibody secretion occurred enumerated. Enumeration can be performed manually or by image recognition software.

Detectable signal generated in such assay systems can be localized in order to facilitate enumeration of secreting cells. Such localized signals can be generated by any suitable means, including fluorescence, phosphorescence, luminescence, emission by radionuclides, and/or enzymatic generation of an at least partially insoluble product (e.g. a chromophore or fluorophore). Localization of a signal near a cell can be construed as secretion of an antibody having the assayed characteristics by that cell. Such cells can determined manually or through the use of an automated system.

In some embodiments secretion of antigen-specific antibody and nonspecific antibody can be determined using duplicate test surfaces/plates. In other embodiments secretion of antigen-specific antibody and nonspecific antibody can be determined using the same test surface by utilizing distinguishable labels. For example, secretion of antigen-specific antibodies can be characterized using a first fluorophore associated with antigen-specific assay performed on the test surface while secretion of antibodies (antigen-specific or otherwise) can be determined using a second fluorophore, where the second fluorophore is distinguishable from the first fluorophore and is associated with a species-specific immunoassay performed on the test surface. Characterization of emissions from the first fluorophore provide characterization of cells secreting antigen-specific antibodies, whereas characterization of emissions from the second fluorophore provide characterization of all cells secreting antibodies. The number of cells secreting nonspecific antibodies can be determined by the difference between these values.

As noted above, methods of the inventive concept are not limited to specific vaccinating species. Suitable vaccines can be directed to viral, bacterial, fungal, autoimmune disease-associated, and/or neoplastic antigens. Examples of vaccines to which methods of the inventive concept can be directed include preventative vaccines, such as those directed to adenovirus, anthrax, botulism, cholera, diphtheria, hepatitis A, hepatitis B, hepatitis C, *Haemophilus influenza* type b, human papillomavirus, seasonal influenza, Japanese encephalitis, measles, Meningococcus, mumps, pertussis, Pneumoccocus, polio, rabies, rotavirus, rubella, shingles, smallpox, tetanus, tuberculosis, typhoid fever, varicella, and/or yellow fever. Further examples of vaccines to which methods of the inventive concept can be directed include therapeutic vaccines, such as vaccines directed to glioblastoma, cervical cancer, skin cancer, lung cancer, breast cancer, head and neck cancer, pancreatic cancer, celiac disease, and/or vulvovaginal candidiasis.

A vaccine preparation to be tested can be polyvalent (i.e. incorporating more than one vaccinating antigen). Examples include childhood MMR vaccine preparations, botulism vaccines, and vaccines directed to seasonal influenza (which generally incorporate viral antigens associated with several different viral strains). In some embodiments the response to each component antigenic species of the polyvalent vaccine preparation can be determined using a different test surface or set of test surfaces. In other embodiments the response to different antigens of a polyvalent vaccine preparation can be characterized using a common test surface or set of test surfaces. For example, in characterizing a polyvalent vaccine preparation that incorporates a first vaccinating antigen and second vaccinating antigen, a test surface can be provided that carries antibodies to both the first and second vaccinating antigens. Treatment of the test surface with the first and second antigens (or analogs thereof) would result in the formation of first and second antibody:antigen complexes on the test surface. Secretion of antibodies to the first vaccinating antigen results in capture of those antibodies proximal to the secreting cell as an antibody:first antigen:antibody complex. Similarly, secretion of antibodies to the second vaccinating antigen results in capture of those antibodies proximal to the secreting cell as an antibody:second antigen:antibody complex. Use of differentiable labels permits separate identification of such complexes and identification of a first set of cells secreting antibodies to the first vaccinating antigen and of a second set of cells secreting antibodies to the second vaccinating antigen utilizing a common test surface. In some embodiments cells secreting nonspecific antibody can be determined on the same test surface as described above, using a third distinguishable label.

Antigenicity and/or potency of a vaccine preparation can be determined by comparing the results obtained with a reference vaccine to those obtained with a trial or unknown vaccine preparation using one or more assays as described above. For example, a series of dilutions (e.g. serial dilutions) of a reference vaccine and a similar or identical set of dilutions prepared from a trial vaccine can be prepared and applied to splenocytes and/or B-cells as described above. The number of cells secreting antigen-specific antibody to cells secreting non-specific antibody can be determined for one or more of these dilutions for both the reference vaccine and the trial vaccine, and the results compared. In a preferred embodiment a ratio between the number of antigen-specific antibody secreting cells and non-specific antibody secreting cells can be used as the basis for such a comparison. Such comparisons can be performed by any suitable method, for example parallel line analysis of the respective dilution:response curves.

Results between a reference vaccine and one or more trial vaccines can be compared by any suitable means, with correspondence between the results for the reference and trial vaccines being indicative of acceptable potency. For example, the dilution corresponding to a half-maximal response (e.g. EC50) for a reference vaccine and a trial vaccine can be compared. In a preferred embodiment a function of the data from two or more dilutions (for example, optical density vs dilution) is obtained for a reference vaccine and a trial vaccine, and the functions are compared. For example, a first slope can be determined for a line drawn between two or more data points representing different dilutions of a reference vaccine and a second slope determined for a line drawn between two or more data points representing different dilutions of a trial vaccine, and the first and second slopes subsequently compared to determine the extent to which they are parallel (for example, by parallel line analysis). Significant deviations from parallelism (e.g. a difference in slope of from about 5%, 10%, 15%, 20%, or 25%) can indicate a significant difference in potency between trial and reference lots of vaccinating composition. If the difference between slopes is found to be within acceptable limits the degree to which they are displaced from one another can be taken into consideration. For example, if the derived lines of dose response curves of test and reference vaccinating compositions are found to be essentially parallel, a displacement along the dilution axis of the dose response curve (typically the x axis) of greater than about 0.2-fold, 0.5-fold, 0.8-fold, 1-fold, 1.2-fold, 1.5-fold, 1.8-fold, 2-fold, 2.5-fold or more dilutions can indicate a significant difference in potency between test and reference compositions. Such differences in potency can be used to determine acceptability and/or dosing dilution of a test vaccine preparation.

In some embodiments such dose/response curves may be nonlinear across a portion of the dilutions tested, in which case an alternative function suitable for nonlinear data (e.g. instant slope at half of the maximum response via 4PL or 5PL fit, etc.) can be utilized. Alternatively, a minimal dilution of a vaccine preparation that produces a half-maximal response can be selected and used as an acceptance criteria.

In some embodiments of the inventive concept a vaccine potency assay can be based on cell-based assays demonstrating a secondary response to immunization. In such embodiments a number of animals (e.g. mice, rabbits, guinea pigs, etc.) are immunized with a vaccine (such as a reference vaccine of known potency), and splenocytes and/or B-cells isolated from the immunized animals to provide a population of primary sensitized cells. Such primary sensitized cells can be obtained and used directly from living animals. In other embodiments primary sensitized cells can be collected and frozen, then thawed prior to use. In some embodiments B-cell populations within collected splenocytes are enriched; in other embodiments one or more specific cell populations (e.g. plasma cells) can be depleted.

Figure 2:
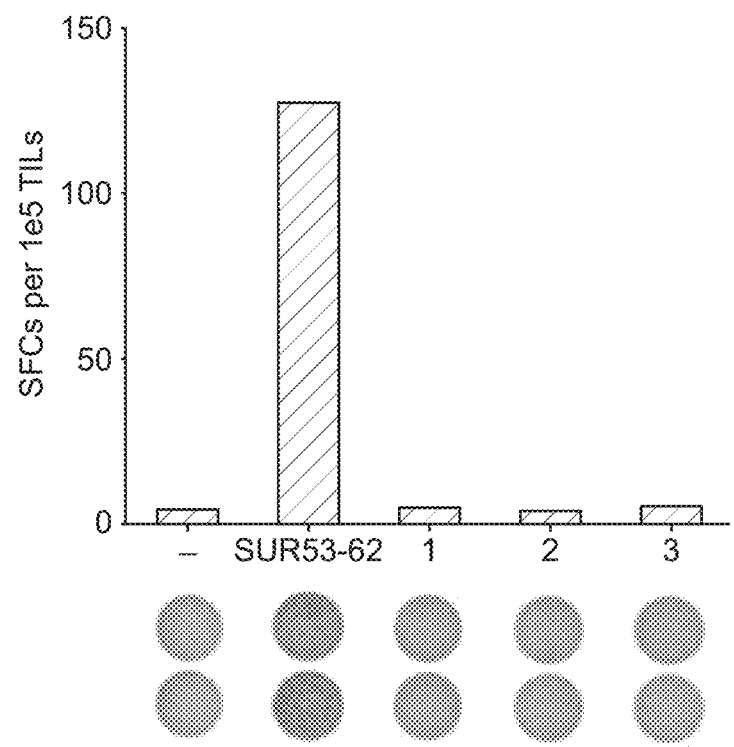
FIG. 2.

Such a preparation of primary sensitized cells can be treated with a series of dilutions of a test vaccine to elicit a specific and/or non-specific immune response. In some embodiments dilutions of a reference vaccine of known potency can be tested in parallel. Immune responses can be characterized as described above. For example, ELISPOT and similar assays directed to specific antigens of the vaccine preparation and to immunoglobulin species can be performed to determine specific and non-specific responses, respectively. A typical antibody plaque immunoassay is depicted schematically in FIG. 1. Typical results for an antibody plaque immunoassay are shown in FIG. 2.

In some embodiments the primary sensitized cells can be treated with the test vaccine prior to application to such an assay. In other embodiments the primary sensitized cells can be treated with the test vaccine at the time the assay is performed or during the performance of the assay (e.g. following dispensing of primary sensitized cells to the wells of an antibody plaque immunoassay plate). Counting of specific and non-specific Ig-secreting cells followed by generation of dose/response curves can provide a measure of potency for the test vaccine. For example, comparison to similar dilutions of a reference vaccine of known potency can provide a relative measure of potency for a test vaccine. While not representing a de novo primary response, the Inventors believe that the secondary response that is characterized has similar relevance to vaccine potency.

Some vaccine preparation are formulated such that some or all of the immunizing antigen is coated or otherwise bound to the surface of adjuvant solids. Aluminum hydroxide hydrogel and CpG oligonucleotides are examples of such adjuvants, and are widely used (for example, in anthrax vaccines). In order to characterize such vaccine preparations the immunizing antigen can be eluted or released from the adjuvant (for instance, through displacement with competing macromolecules, pH shift, electroelution, etc.) prior to application to the primary sensitized cells in order to improve accessibility and/or facilitate diffusion during the assay. In other embodiments such vaccine preparations can be tested as formulated.

In one example of a method of the inventive concept mice (or guinea pigs) are immunized with a reference batch of anthrax vaccine to generate sensitized splenocytes. Splenocytes are subsequently isolated from the immunized animals and, in some embodiments, particular B cell populations are enriched. Splenocytes (which can be enriched or depleted) are plated in 96-well plates that are prepared for use with an antibody plaque immunoassay such as Enzyme-Linked ImmunoSpot (ELISpot). In some embodiments the splenocytes are re-activated with dilutions of either a test vaccine or a reference vaccine prior to introduction to an antibody plaque immunoassay plate or similar methodology. In other embodiments the splenocytes are re-activated at the time of or following introduction to an antibody plaque immunoassay plate or similar methodology. One set of plates can be configured to measure antigen-specific immunoglobulin secretion (for example, by coating with one or more immunizing antigens). A second set of plates can be configured to measure total (specific and non-specific) immunoglobulin (Ig) secretion (for example, by coating with one or more Ig-specific antibodies). Serial dilutions of a vaccine test sample are then applied to the plates containing the cells along with serial dilutions of a reference vaccine sample. Alternatively splenocytes (or isolates) can be incubated with dilutions of test and reference vaccines prior to application to the antibody plaque immunoassay plates. The plates are then incubated for a period of time sufficient for vaccine preparations to interact with the splenocytes, activating specific and/or non-specific immune responses that result in the secretion of Ig.

The number of Ig-secreting cells is correlated with the effective dose of vaccine, which is in turn a function of vaccine potency. Once the assays are completed the number of Ig-secreting cells, both antigen-specific and nonspecific or not, per well are counted, using manual or automated methods. It should be appreciated that, since antigen-specific Igs are also identified by the nonspecific antibody plaque immunoassay plate, that the number of nonspecifically activated cells is represented by the difference in count between the nonspecific and antigen-specific antibody plaque immunoassay plates. Dose-response curves (e.g. number of Ig-secreting cells vs. vaccine dose) are constructed for the test and reference samples. The dose-response curves of the test and reference samples are can then be modeled with an appropriate equation (e.g. a 4-PL or 5-PL asymmetric curve fit) and the relative potency of the test can be calculated using a parallel-line method.

Figure 3:
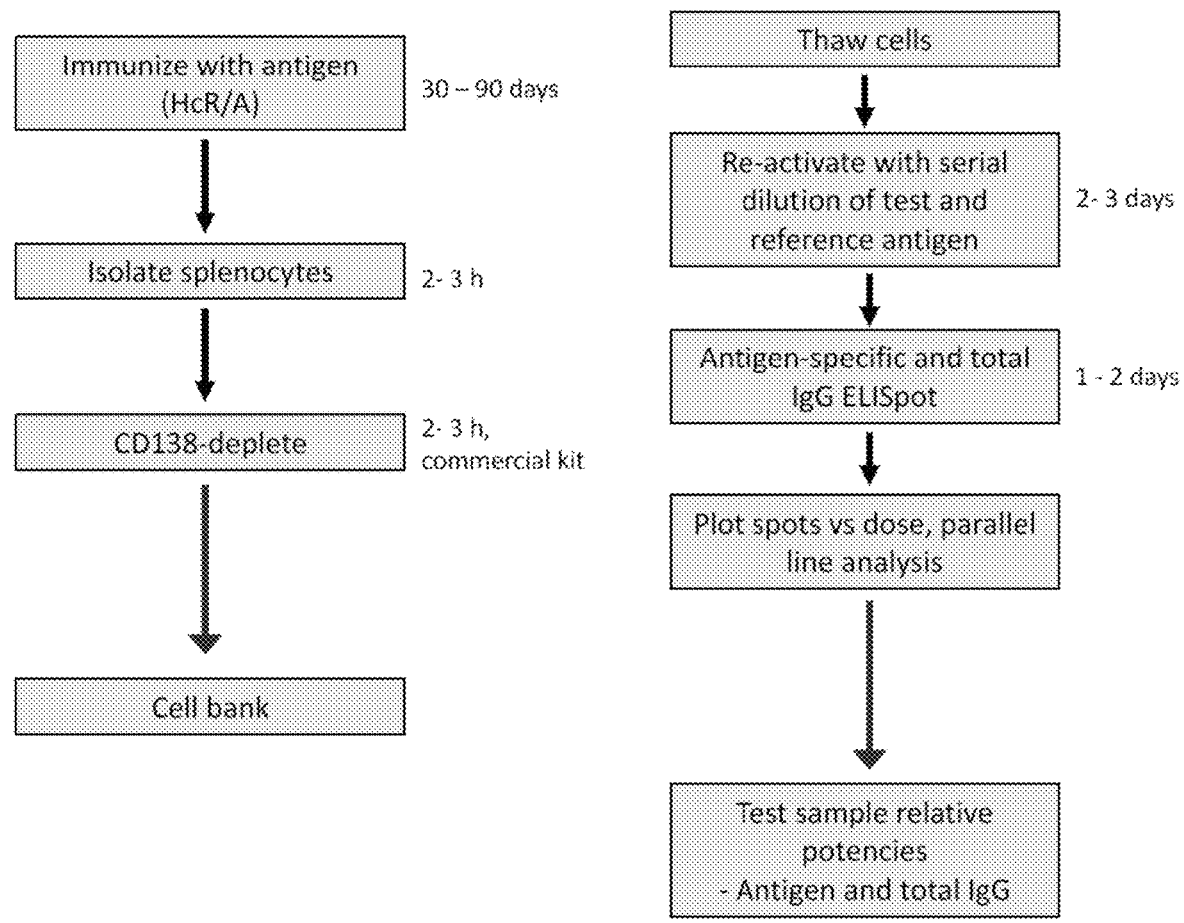
FIG. 3.

An exemplary protocol for a splenocyte assay for determining vaccine potency is shown in FIG. 3. As shown on the left side of FIG. 3, in such a testing protocol mice are immunized with the vaccinating antigen (e.g. HcR/A), and splenocytes are subsequently isolated from harvested spleens. The splenocytes are depleted of CD138 positive cells (for example, using a commercial kit), aliquoted, and frozen to generate a cell bank. In order to perform the assay (as shown on the right side of FIG. 3) cells from the cell bank are thawed, then reactivated by exposure to serial dilutions of a reference antigen (e.g. a reference vaccine) and of a test antigen (e.g. a vaccine preparation being evaluated). Following reactivation antigen-specific and total species-specific antibody being secreted by the cells is characterized; in this example characterization is performed using an antigen-specific and an IgG-specific antibody plaque immunoassay plates. The number and/or density of spots in the test wells is recorded and dose/response curves relative to the control and test antigen preparations are generated. These dose response curves are compared (for example, by parallel line analysis) to provide a measure of the potency of the test antigen preparation relative to the control antigen preparation.

Figure 4A:
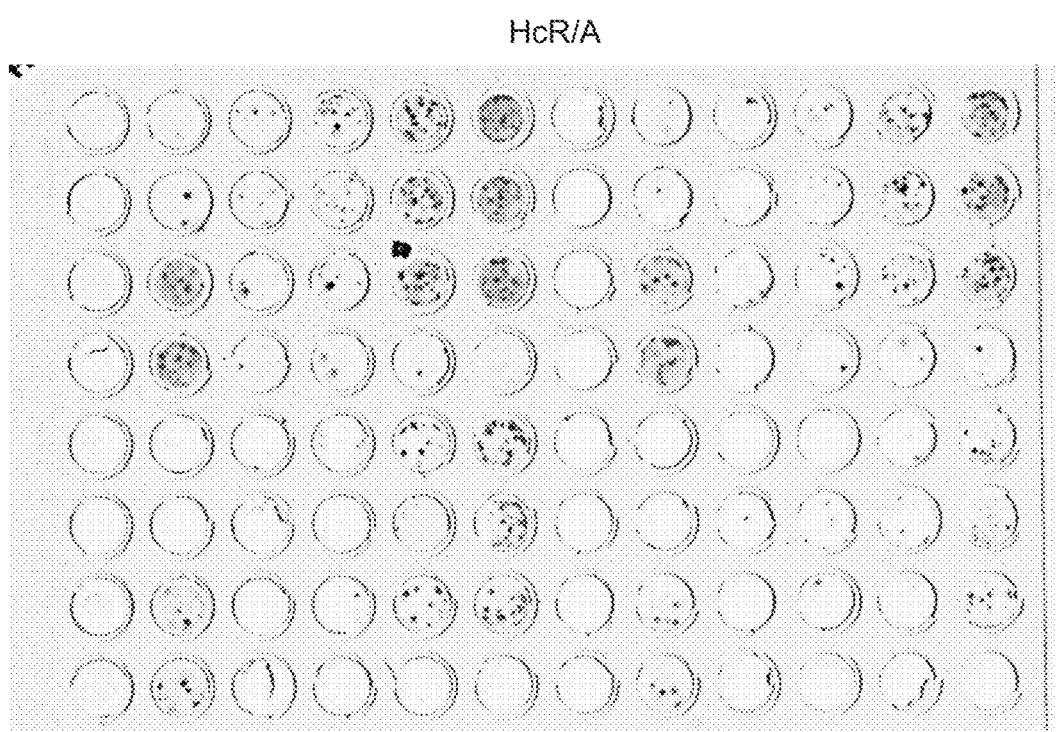
FIG. 4A.
Figure 4B:
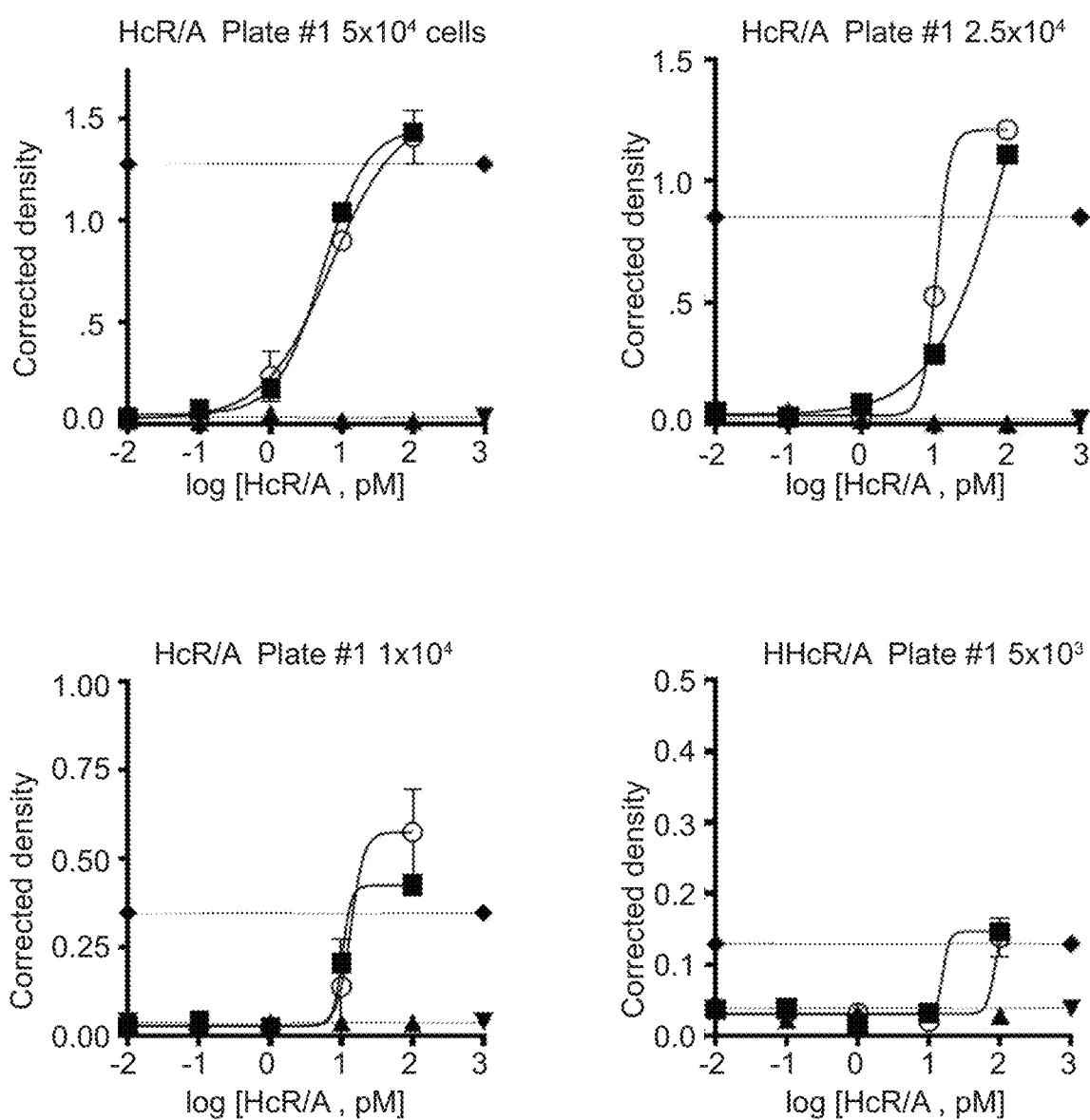
FIG. 4B.
Figure 4C:
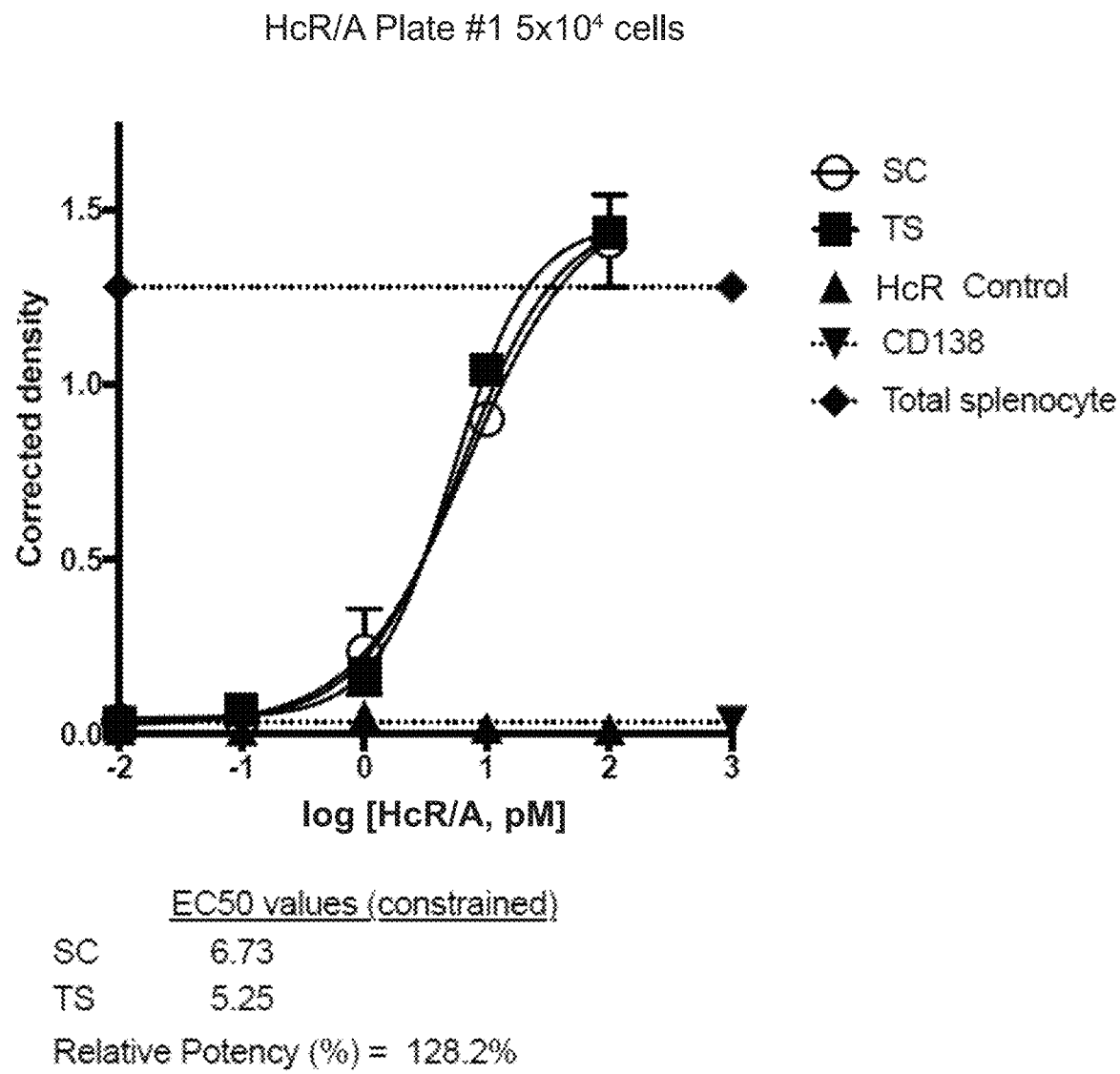
FIG. 4C.

FIG. 4A shows an image of an ELISpot test plate for HcR/A antigen. Wells in which splenocytes are responsive to HcR/A show discrete, high optical density spots at the cell's location. These become nearly confluent at high concentrations/low dilutions. The number and/or density of these spots can be quantified and compared to the dilution of HcR/A antigen containing preparation applied, as shown in FIG. 4B. As shown, dose response curves provide a greater dynamic range at greater cell densities. FIG. 4C shows the dose response curve obtained at a coating density of $5 \times 10^4$ cells in greater detail and provides a comparison between the test (TS) and reference (SC) antigen preparations in terms of a calculated $EC_{50}$ and relative potency.

Figure 5A:
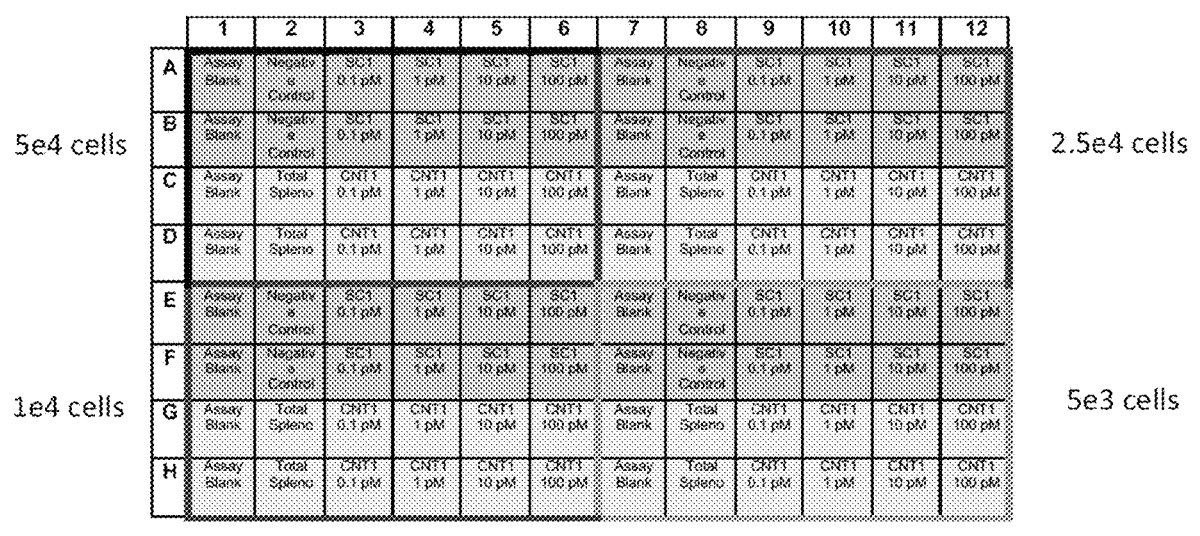
Figure 5B:
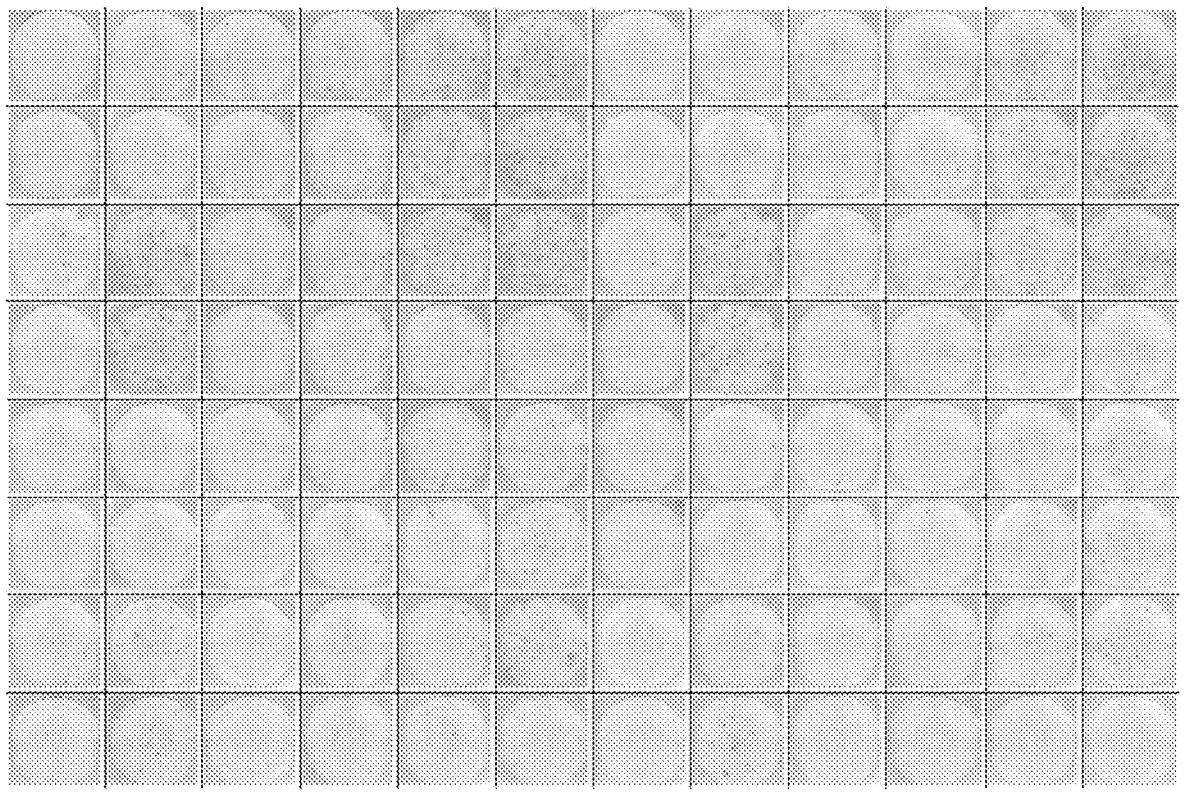
FIG. 5B.
Figure 5C:
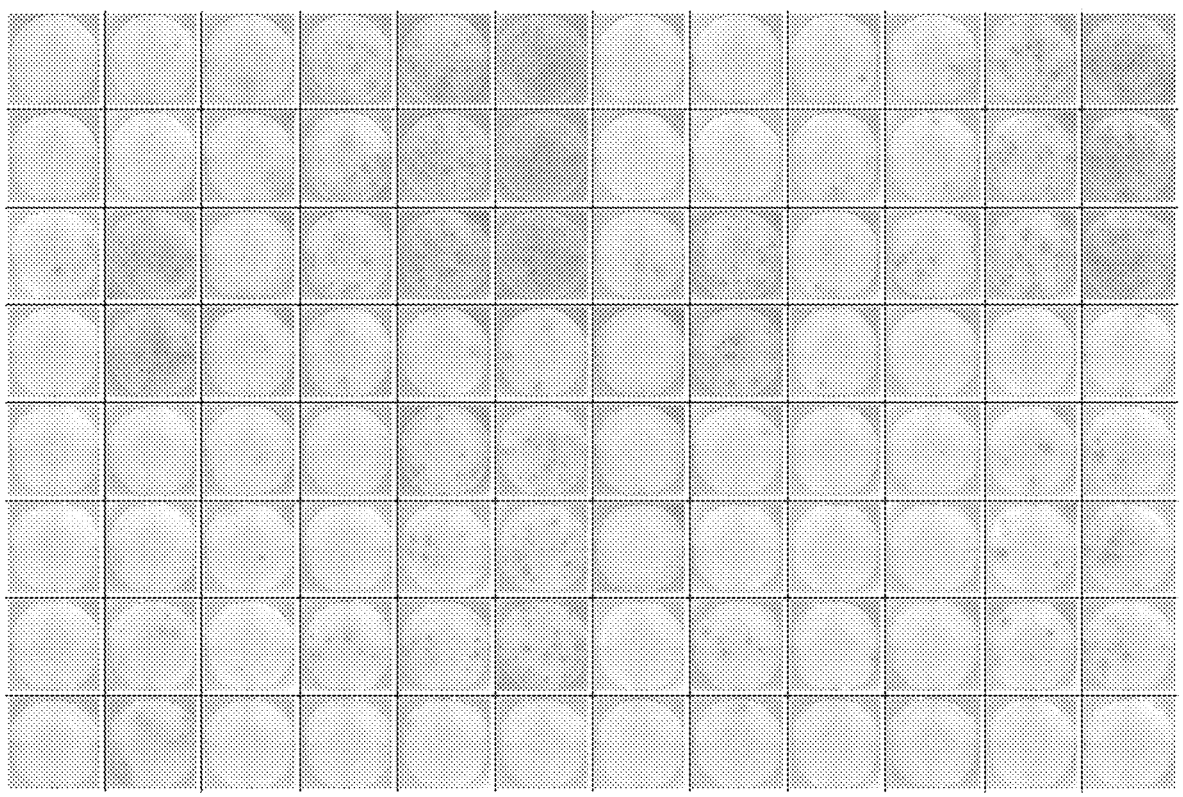
FIG. 5C.
Figure 5D:
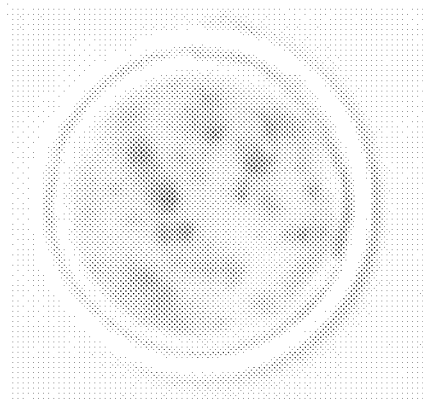
FIG. 5D.
Figure 5E:
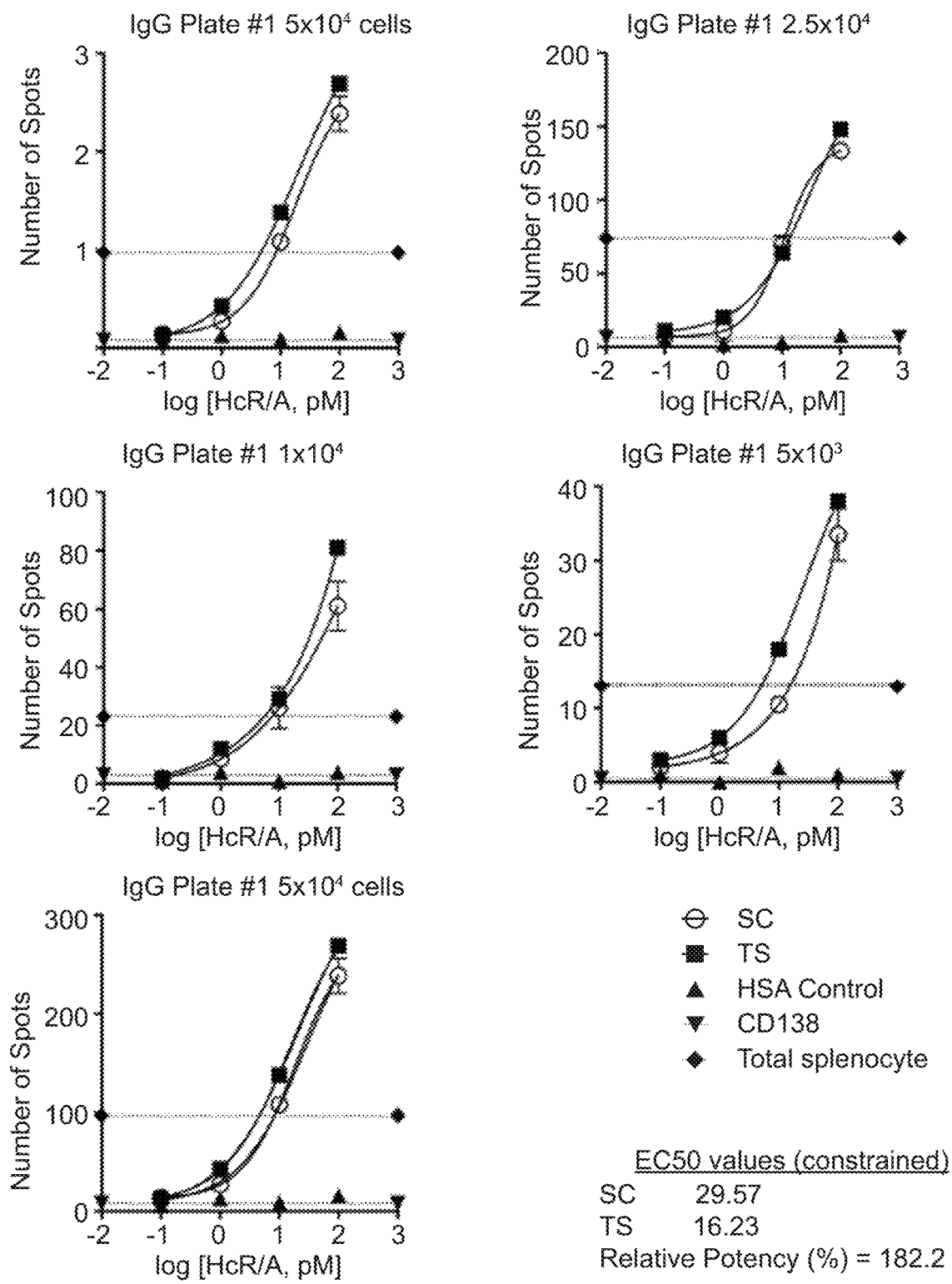
FIG. 5E.
Figure 5F:
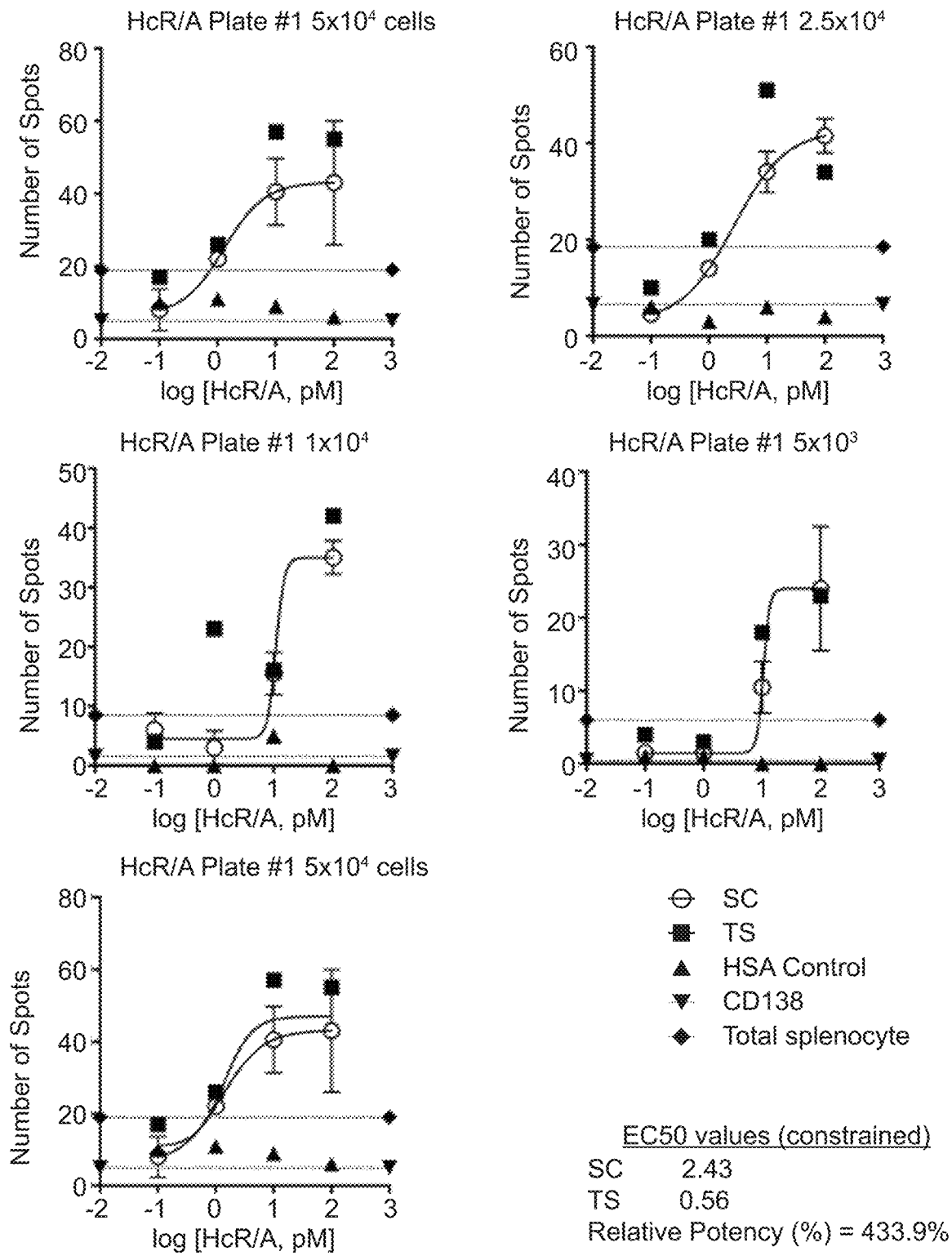
FIG. 5F.

As noted above, characterization of an immune response generated by a vaccine preparation can be characterized in terms of both the production of antigen-specific antibodies and the proportion of antigen-specific antibodies generated relative to the total production of antibodies of a particular type. Accordingly, antigen specific and antibody specific antibody plaque immunoassay plates or similar technologies can be applied in parallel to banked splenocytes in order to more fully characterize vaccine potency. An example of an antibody plaque immunoassay plate layout incorporating different splenocytes coating densities is shown in FIG. 5A. FIG. 5B shows an image of an antibody plaque immunoassay plate prepared as above, in which IgG secretion from the splenocytes is visualized. FIG. 5C shows an image of an antibody plaque immunoassay plate prepared as above, in which HcR/A specific antibody secretion from the splenocytes is visualized. FIG. 5D provides a magnified view of an individual well of an antibody plaque immunoassay plate in which HcR/A specific antibody secretion by splenocytes coated at $5 \times 10^4$ cells/well and stimulated with 100 pM antigen. As noted above, dose response curves can be derived for either or both of antigen specific response and antibody species response. FIG. 5E shows dose response curves obtained from an antibody plaque immunoassay plate prepared as shown in FIG. 5A and characterized for IgG secretion. FIG. 5F shows dose response curves obtained from an antibody plaque immunoassay plate prepared as shown in FIG. 5A and characterized for HcR/A specific antibody secretion.

Figure 6B:
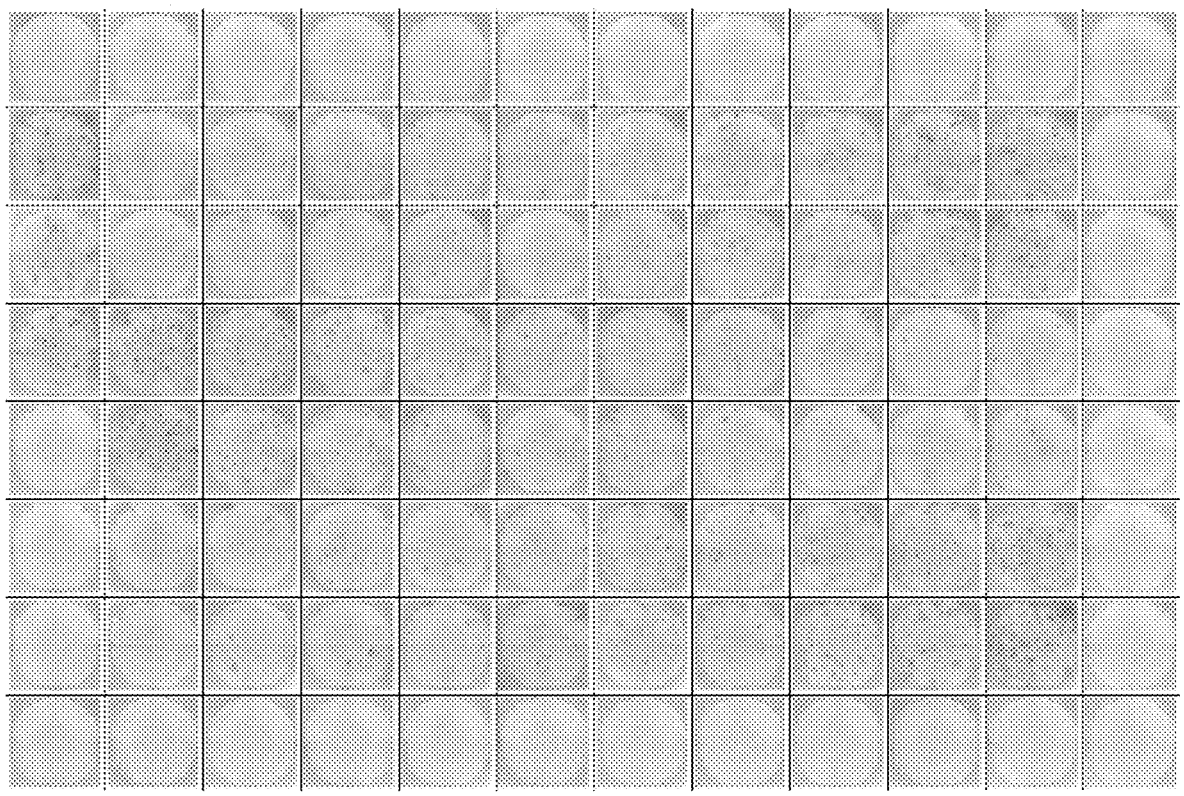
FIG. 6B.

Another example of a vaccine potency assay of the inventive concept is shown in FIGS. 6A to 6E. In these studies RBC lysed splenocytes were depleted of CD138 positive cells using a StemCell Technologies™ PE selection kit and an anti-CD138, PE-labeled antibody prior to suspension at $7.5 \times 10^5$ cells per well of an incubation plate. Antigen preparations were diluted and applied to the plates, which were then incubated at 37° C. and 5% $CO_2$ for 48 hours. On day 2 PVDF plates were prepared by coating with either 40 µg/mL HcR/A or 20 µg/mL anti-murine IgG at 4° C. overnight, then blocked with EL4-B5 media for 2 hours at 37° C. and 5% $CO_2$. On day 3 activated splenocytes were harvested from the incubation plate and resuspended at $10^6$ cells per mL, then pipette into the blocked PVDF plates at either $5\times10^4$ or $2.5\times10^4$ cells per well, the incubated overnight at 37° C. and 5% $CO_2$. On day 4 cells were removed from the PVDF plates by washing with PBS (3×) and with PBST (3×). The PVDF plates were then incubated with 80 µL/well 1:5,000 anti-murine IgG-HRP for 8 hours at 4° C. After washing the plates with PBS-T (3×) and PBS (3×) 100 µL of AEC precipitable substrate was added to each well and incubated for 5 minutes at ambient temperature. The reaction was stopped by washing the plates with tap water and allowing them to dry overnight in the dark prior to image acquisition and analysis. FIG. 6A shows an exemplary plate layout for such a study.

Figure 6C:
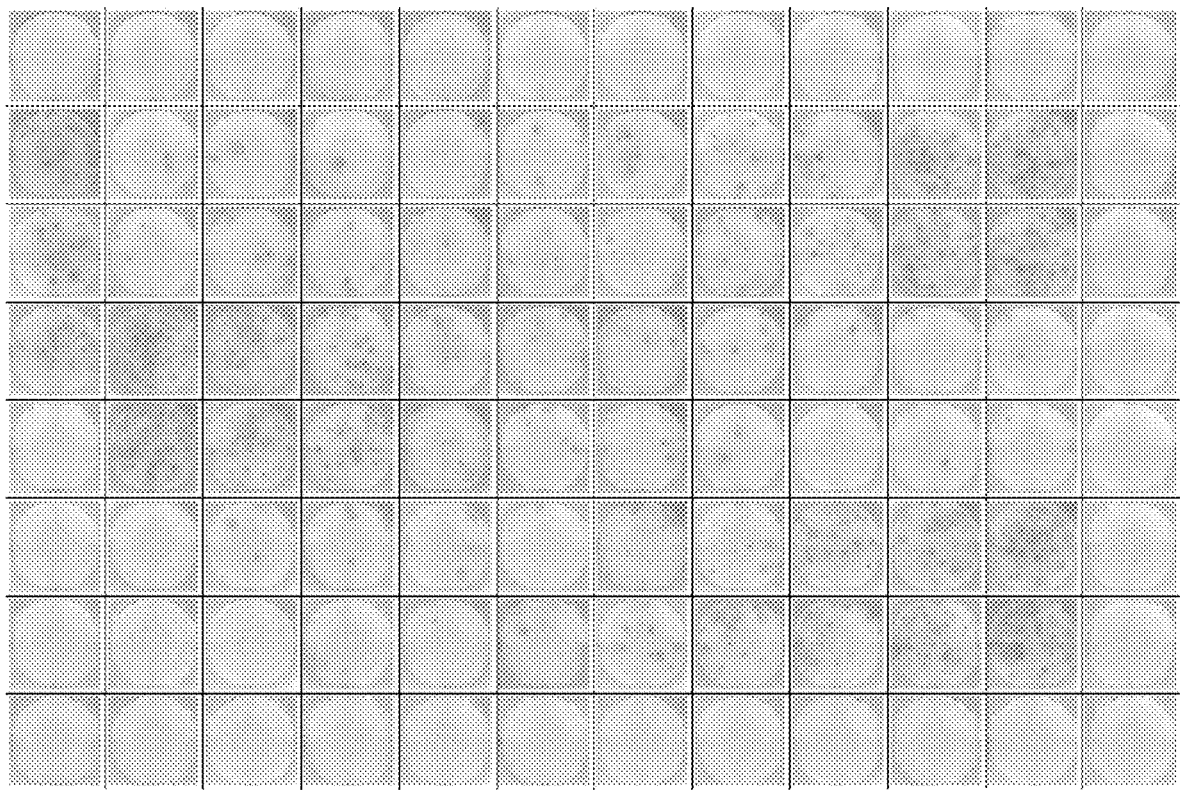
FIG. 6C.

FIG. 6B shows an image of a typical plate used for characterizing IgG secretion from activated splenocytes (i.e. coated with anti-murine IgG) where the contents of the plate are arranged as shown in FIG. 6A. FIG. 6C shows a similar image obtained for a typical plate used for characterizing HcR/A antigen specific antibody secretion by activated splenocytes from a plate arranged in the same manner.

Figure 6D:
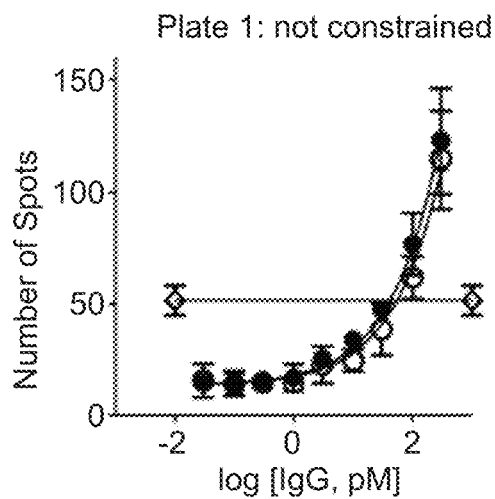
FIG. 6D.
Figure 6D:
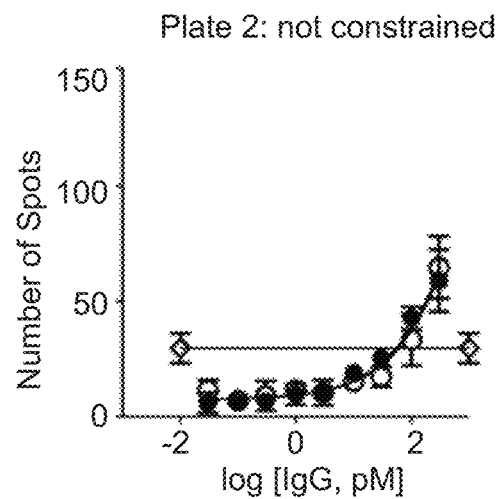
Figure 6D:
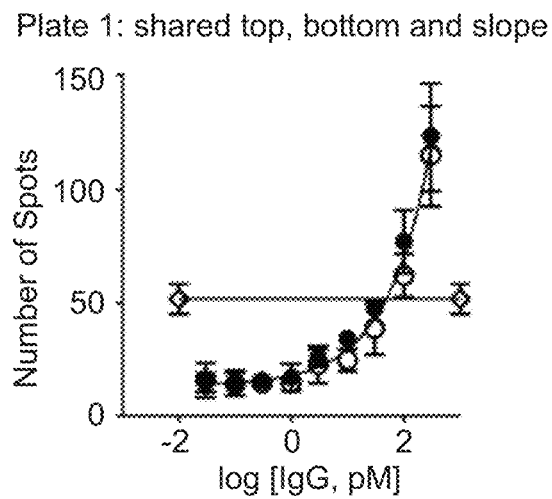
Figure 6D:
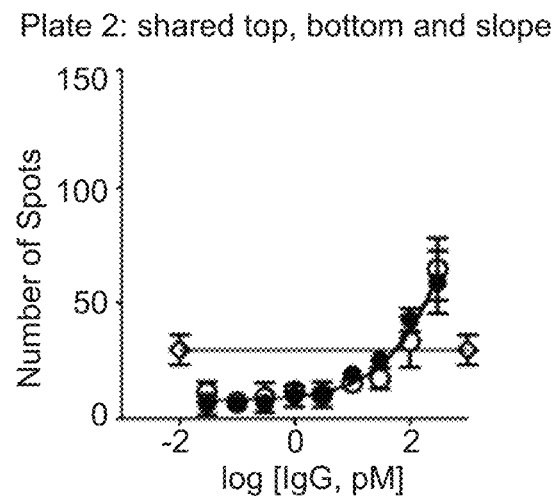
Figure 6E:
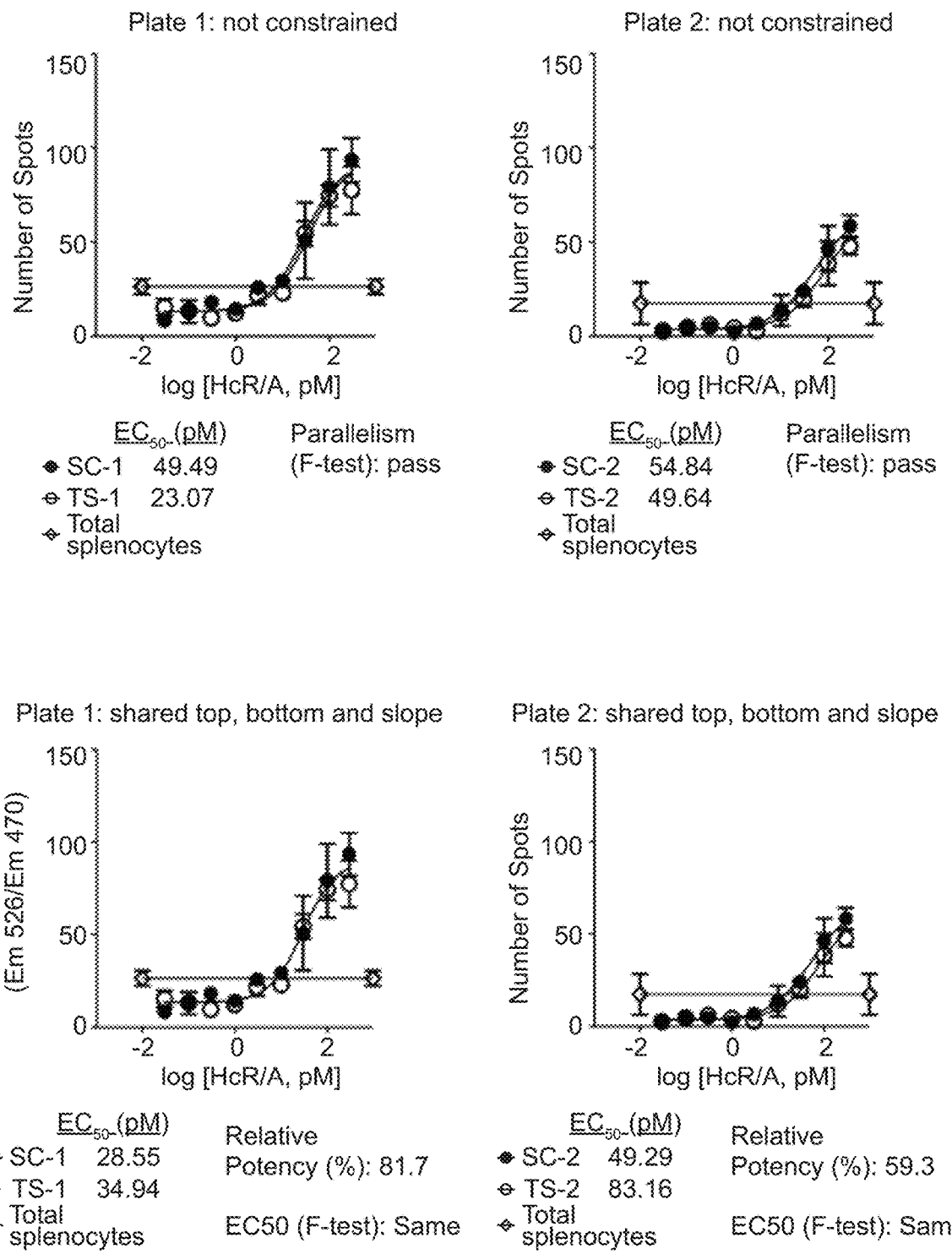
FIG. 6E.

As noted above, potency in terms of both IgG response and antigen-specific response can be characterized by quantitation of spot number and/or density from such images. FIG. 6D shows dose response curves relative to dilution of the antigenic preparation, calculated $EC_{50}$, and calculated relative potency for the IgG response of activated splenocytes characterized using a plate layout as shown in FIG. 6A. FIG. 6E shows dose response curves relative to dilution of the antigenic preparation, calculated $EC_{50}$, and calculated relative potency for the HRC/A specific antibody response of activated splenocytes characterized using a plate layout as shown in FIG. 6A.

Figure 7B:
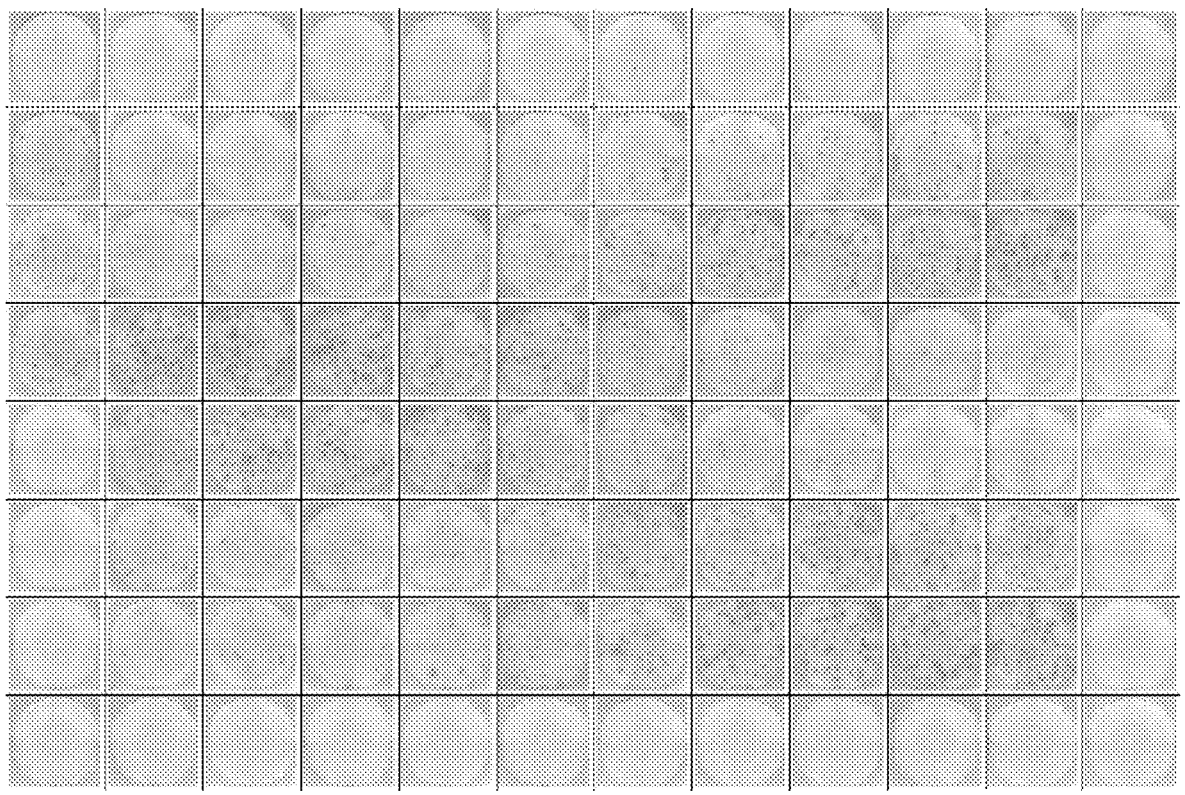
FIG. 7B.

FIGS. 7A to 7E show the results of studies performed as described above for FIGS. 6A to 6E, with C138 depleted splenocytes activated with antigen dilutions at $10^6$, $7.5\times10^5$, or $5\times10^5$ cells per mL. The plate format used is shown in FIG. 7A.

Figure 7C:
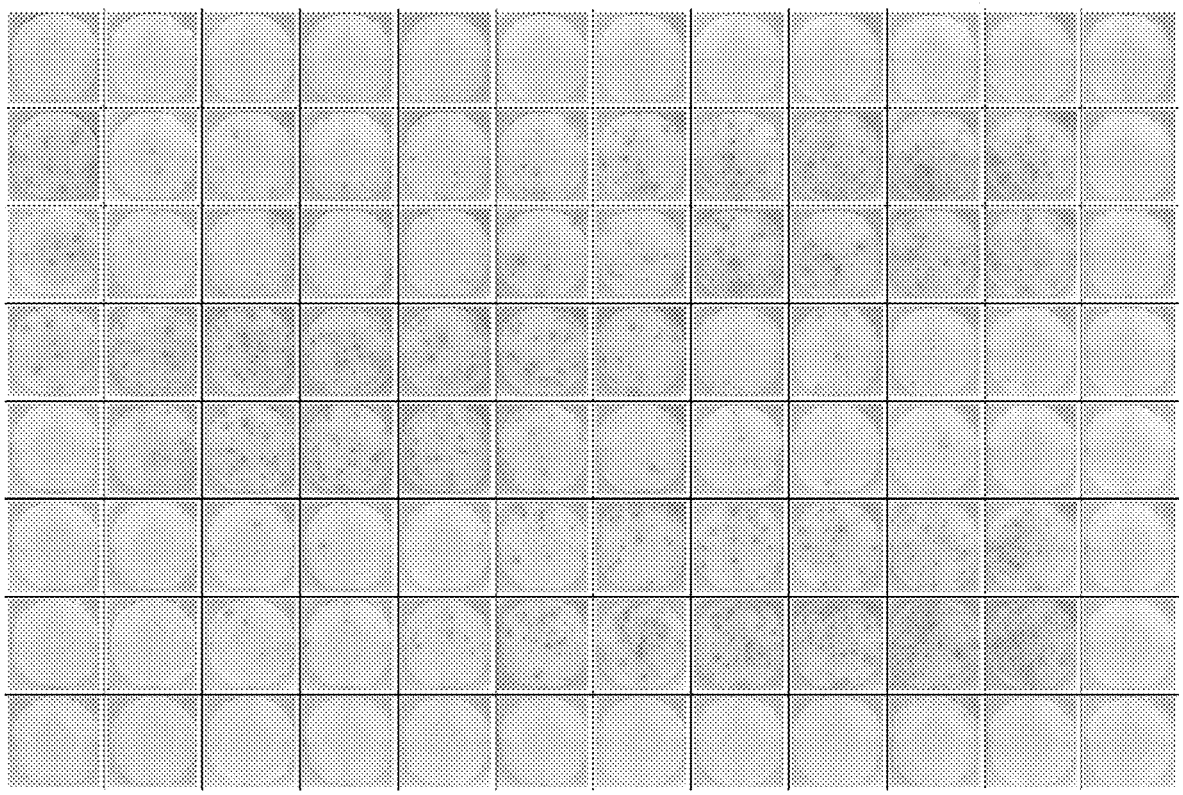
FIG. 7C.

FIG. 7B shows an image of a typical antibody plaque immunoassay plate used for characterizing IgG secretion from activated splenocytes (i.e. coated with anti-murine IgG) where the contents of the plate are arranged as shown in FIG. 7A. FIG. 7C shows a similar image obtained for a typical antibody plaque immunoassay plate used for characterizing HcR/A antigen specific antibody secretion by activated splenocytes from a plate arranged in the same manner.

Figure 7D:
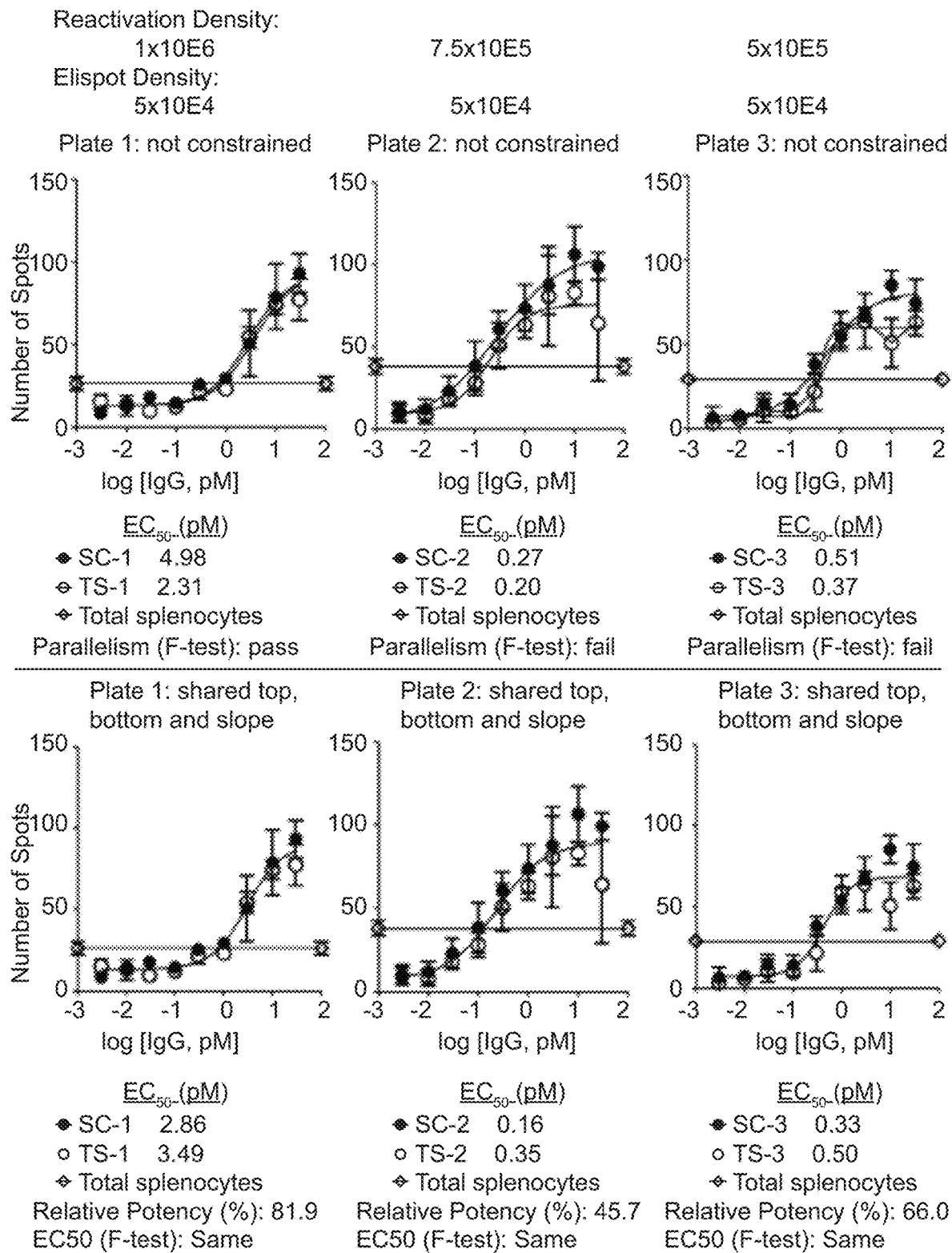
FIG. 7D.
Figure 7E:
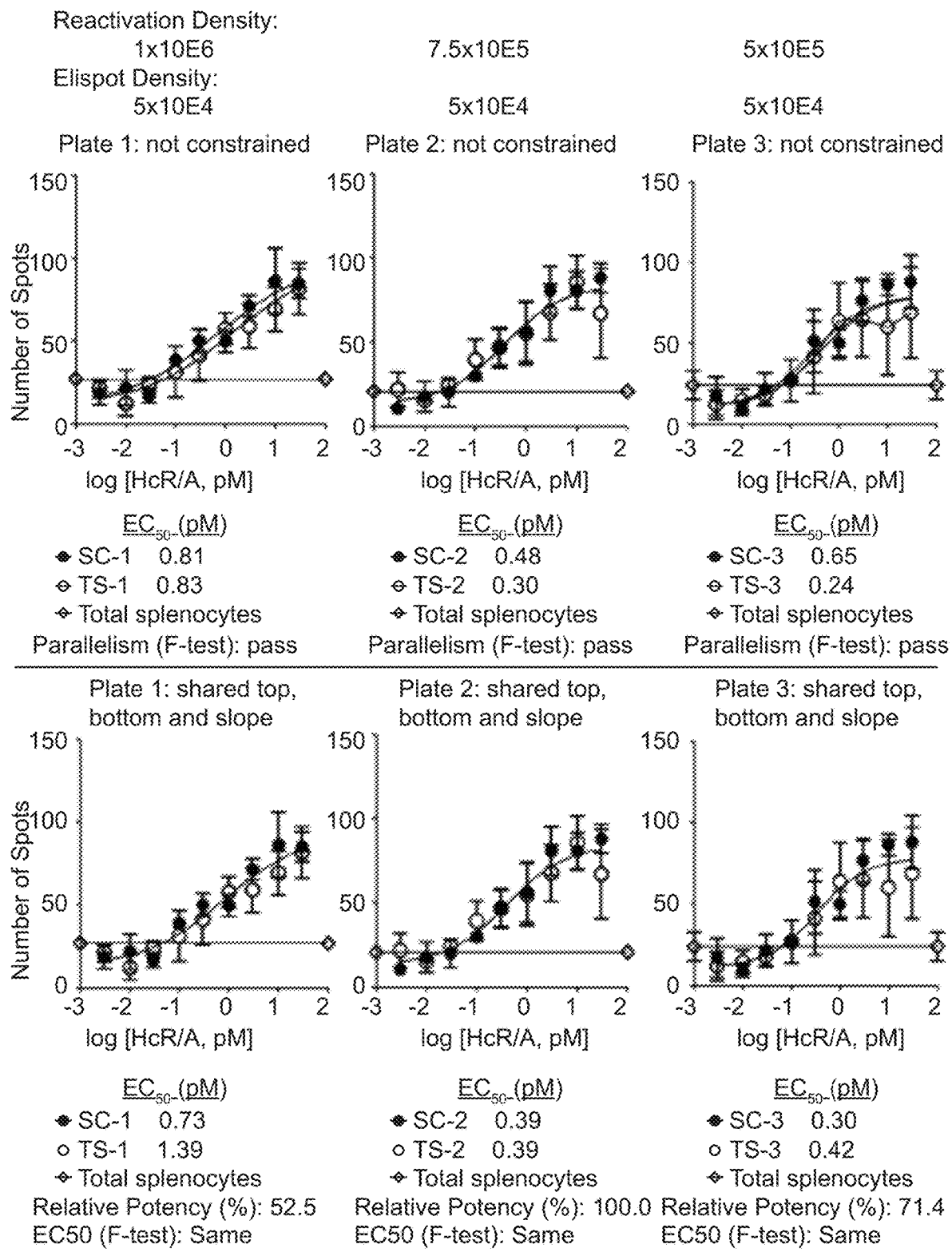
FIG. 7E.

As noted above, potency in terms of both IgG response and antigen-specific response can be characterized by quantitation of spot number and/or density from such images. FIG. 7D shows dose response curves relative to dilution of the antigenic preparation, calculated $EC_{50}$, and calculated relative potency for the IgG response of splenocytes activated at different splenocytes concentrations and characterized using an antibody plaque immunoassay plate layout as shown in FIG. 7A. FIG. 7E shows dose response curves relative to dilution of the antigenic preparation, calculated $EC_{50}$, and calculated relative potency for the HcR/A specific antibody response of splenocytes activated at different concentrations and characterized using an antibody plaque immunoassay plate layout as shown in FIG. 7A.

Although the examples provided above utilized separate antibody plaque immunoassay plates for total IgG secretion and antigen specific antibody secretion, it should be appreciated that in some embodiments such measurements could be obtained from a single antibody plaque immunoassay plate through the use of immunoglobulin-specific and antigen-specific secondary antibodies in the same test well in combination with differential labeling. Similarly, although HRP conjugates were utilized for detection purposes, it should be appreciated that other detectable labels including alternative enzymes (for example, alkaline phosphatase), fluorophores, chromophores, lumiphores, colloidal gold, and/or dyed microparticles can be utilized.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of characterizing specificity of a vaccine preparation to be characterized, wherein the vaccine preparation to be characterized comprises an antigen, comprising:
    vaccinating an animal with a reference vaccine comprising the antigen and that is known to be immunogenic and have acceptable potency to generate splenocytes and B cells;
    collecting said splenocytes or B cells from the animal;
    contacting a first portion of said splenocytes or B cells with a first set of dilutions, wherein the first set of dilutions is prepared from the reference vaccine;
    contacting a second portion of said splenocytes or B cells with a second set of dilutions, wherein the second set of dilutions is prepared from the vaccine preparation to be characterized;
    following contacting with the first set of dilutions, enumerating a first number of cells that express antibodies specific for the antigen, and a second number of cells expressing nonspecific antibodies, and calculating a first ratio between the first number and the second number for each of the respective first set of dilutions;
    generating a first specificity response curve from values of said first ratios and corresponding dilutions of the first set of dilutions;
    following contact with the second set of dilutions, enumerating a third number of cells expressing antibodies specific for the first antigen and a fourth number of expressing nonspecific antibodies, and calculating a second ratios between the third number and the fourth number for each of the second set of dilutions;
    generating a second specificity response curve from values of said second ratios and corresponding dilutions of the second set of dilutions;
    comparing the first specificity response curve to the second specificity response curve,
    wherein comparing comprises:

determining a first characterizing dilution of the reference vaccine and a second characterizing dilution of the vaccine preparation to be characterized at which corresponding slopes tangent the first and second specificity dose response curves, respectively, are parallel to one another, by parallel line analysis of the first and second specificity dose response curves; and determining a displacement between the first characterizing dilution and the second characterizing dilution, wherein a displacement greater than 0.2-fold is indicative of a significant difference in specificity between the reference vaccine and the vaccine preparation.

2. The method of claim 1, wherein the first number is determined using a first immunoassay comprising a first label, and the first second number is determined using a second immunoassay that utilizes a second label, wherein the first label and second label are distinguishable from one another.

3. The method of claim 2, wherein the first immunoassay and the second immunoassay are antibody plaque assays.

4. The method of claim 1, wherein the vaccine preparation to be characterized comprises a preventative vaccine.

5. The method of claim 4, wherein the antigen is from at least one of the group consisting of adenovirus, anthrax, botulism, cholera, diphtheria, hepatitis A, hepatitis B, hepatitis C, *Haemophilus influenza* type b, human papillomavirus, seasonal influenza, Japanese encephalitis, measles, Meningococcus, mumps, pertussis, Pneumoccocus, polio, rabies, rotavirus, rubella, shingles, smallpox, tetanus, tuberculosis, typhoid fever, varicella, and yellow fever.

6. The method of claim 1, wherein the vaccine preparation to be characterized comprises a therapeutic vaccine.

7. The method of claim 6 wherein the antigen is from at least one of the group consisting of glioblastoma, cervical cancer, skin cancer, lung cancer, breast cancer, head and neck cancer, pancreatic cancer, celiac disease, and vulvovaginal candidiasis.

8. A method of characterizing potency of a vaccine preparation to be characterized, wherein the vaccine preparation to be characterized comprises an antigen, comprising:
    vaccinating an animal with a reference vaccine comprising the antigen and that is known to immunogenic and have acceptable potency to generate splenocytes and B cells;
    collecting splenocytes or B cells from the animal;
    contacting a first portion of said splenocytes or B cells with a first set of dilutions prepared from the reference vaccine;
    contacting a second portion of said splenocytes or B cells with a second set of serial dilutions prepared from the vaccine preparation to be characterized;
    following contacting with the first set of dilutions, enumerating a first number of cells that express antibodies specific for the antigen for each of the first set of dilutions;
    generating a first dose response curve from values of the first number and corresponding dilutions of the first set of dilutions;
    following contacting with the second set of dilution, enumerating a second number of cells expressing antibodies specific for the antigen for each of the second set of dilutions;
    generating a second dose response curve from values of the second number and corresponding dilutions of the second set of dilutions; and
    comparing the first response curve to the second dose response curve,
    wherein comparing comprises:
    determining a first characterizing dilution of the reference vaccine and a second characterizing dilution of the vaccine preparation to be characterized at which corresponding slopes tangent the first and second dose response curves, respectively, are parallel to one another, by parallel line analysis of the first and second dose response curves; and
    determining a displacement between the first dilution and the second dilution, wherein a displacement greater than 0.2-fold is indicative of a significant difference in potency between the reference vaccine and the vaccine preparation.

9. The method of claim 8, wherein the first number and the second number are determined using first and second antibody plaque assays, respectively.

10. The method of claim 8, wherein the vaccine preparation to be characterized comprises a preventative vaccine.

11. The method of claim 10, wherein the antigen is at least one of the group consisting of adenovirus, anthrax, botulism, cholera, diphtheria, hepatitis A, hepatitis B, hepatitis C, *Haemophilus influenza* type b, human papillomavirus, seasonal influenza, Japanese encephalitis, measles, Meningococcus, mumps, pertussis, Pneumoccocus, polio, rabies, rotavirus, rubella, shingles, smallpox, tetanus, tuberculosis, typhoid fever, varicella, and yellow fever.

* * * * *